US008971984B2

(12) United States Patent
Freeman et al.

(10) Patent No.: US 8,971,984 B2
(45) Date of Patent: Mar. 3, 2015

(54) HYPERSPECTRAL TECHNOLOGY FOR ASSESSING AND TREATING DIABETIC FOOT AND TISSUE DISEASE

(75) Inventors: Jenny E. Freeman, Weston, MA (US); Svetlana V. Panasyuk, Lexington, MA (US); Michael J. Hopmeier, Mary Esther, FL (US); Derek Brand, Brighton, MA (US); Kevin Schomacker, Maynard, MA (US)

(73) Assignee: Hypermed Imaging, Inc., Greenwich, CT (US)

( * ) Notice: Subject to any disclaimer, the term of this patent is extended or adjusted under 35 U.S.C. 154(b) by 1249 days.

(21) Appl. No.: 11/507,043

(22) Filed: Aug. 21, 2006

(65) Prior Publication Data

US 2007/0038042 A1 Feb. 15, 2007

Related U.S. Application Data

(63) Continuation-in-part of application No. 11/396,941, filed on Apr. 4, 2006.

(60) Provisional application No. 60/667,677, filed on Apr. 4, 2005, provisional application No. 60/785,977, filed on Mar. 27, 2006, provisional application No. 60/709,422, filed on Aug. 19, 2005.

(51) Int. Cl.
*A61B 5/00* (2006.01)
*G01N 21/47* (2006.01)
(Continued)

(52) U.S. Cl.
CPC ............ *G01N 21/474* (2013.01); *A61B 5/1036* (2013.01); *A61B 5/14551* (2013.01); *A61B 5/412* (2013.01); *A61B 5/445* (2013.01); *A61B 5/447* (2013.01); *G01N 21/31* (2013.01);
(Continued)

(58) Field of Classification Search
None
See application file for complete search history.

(56) References Cited

U.S. PATENT DOCUMENTS 4,610,253 A * 9/1986 Rosenberg ........................ 607/1
4,647,918 A 3/1987 Goforth
(Continued)

FOREIGN PATENT DOCUMENTS

WO WO 2006/058306 6/2006

OTHER PUBLICATIONS

Mak et al., "State-of-the-art research in lower-limb prosthetic biomechanics-socket interface: A review". Journal of Rehabilitation Research and Development. vol. 38 No. 2, Mar./Apr. 2001. pp. 161-174.*

(Continued)

*Primary Examiner* — Long V Le
*Assistant Examiner* — Colin T Sakamoto
(74) *Attorney, Agent, or Firm* — Brett A. Lovejoy; Andrew A. Antczak; Morgan, Lewis & Bockius, LLP

(57) ABSTRACT

This invention relates generally to an index map comprising both pressure and perfusion information from a diabetic patient foot for the purpose of treatment. The index map may also be a map of perfusion and/or metabolism of the tissue (reflecting oxygen delivery and oxygen extraction), obtained by thermal imaging, hyperspectral imaging, or duplex ultrasound, MRA, CT or laser Doppler imaging. This information aids treatment in prevention of diabetic foot ulceration and amputation and in treatment of tissue compromise to prevent tissue loss in other body regions.

22 Claims, 5 Drawing Sheets

(51) Int. Cl.
| | |
|---|---|
| A61B 5/103 | (2006.01) |
| A61B 5/1455 | (2006.01) |
| G01N 21/31 | (2006.01) |
| G01N 21/49 | (2006.01) |
| A61B 5/026 | (2006.01) |
| G01N 21/359 | (2014.01) |

(52) U.S. Cl.
CPC .............. *G01N21/49* (2013.01); *A61B 5/7275* (2013.01); *A61B 5/0261* (2013.01); *A61B 2562/0233* (2013.01); *A61B 2562/046* (2013.01); *G01N 21/4795* (2013.01); *G01N 2021/3144* (2013.01); *G01N 2021/4709* (2013.01); *G01N 21/359* (2013.01)
USPC ........... 600/407; 600/473; 600/475; 600/476; 600/477

(56) References Cited

U.S. PATENT DOCUMENTS

| | | | |
|---|---|---|---|
| 4,805,016 | A | 2/1989 | Kato |
| 5,088,503 | A | 2/1992 | Seitz |
| 5,349,954 | A | 9/1994 | Tiemann et al. |
| 5,539,517 | A | 7/1996 | Cabib et al. |
| 5,566,473 | A | 10/1996 | Salminen |
| 5,642,096 | A | 6/1997 | Leyerer et al. |
| 5,645,081 | A * | 7/1997 | Argenta et al. ............... 128/897 |
| 5,722,287 | A | 3/1998 | Forstein |
| 5,782,770 | A | 7/1998 | Mooradian et al. |
| 5,995,645 | A | 11/1999 | Soenksen et al. |
| 6,104,939 | A | 8/2000 | Groner et al. |
| 6,122,846 | A | 9/2000 | Gray et al. |
| 6,246,301 | B1 | 6/2001 | Sogo et al. |
| 6,556,853 | B1 | 4/2003 | Cabib et al. |
| 6,587,711 | B1 | 7/2003 | Alfano et al. |
| 6,640,130 | B1 | 10/2003 | Freeman et al. |
| 6,640,132 | B1 | 10/2003 | Freeman et al. |
| 6,741,884 | B1 | 5/2004 | Freeman et al. |
| 6,750,964 | B2 | 6/2004 | Levenson et al. |
| 6,810,279 | B2 | 10/2004 | Mansfield et al. |
| 6,918,883 | B2 | 7/2005 | Horton et al. |
| 6,937,885 | B1 | 8/2005 | Lewis et al. |
| 7,013,172 | B2 | 3/2006 | Mansfield et al. |
| 7,166,852 | B2 | 1/2007 | Saracen et al. |
| 2001/0036304 | A1 | 11/2001 | Yang et al. |
| 2002/0057431 | A1 | 5/2002 | Fateley et al. |
| 2002/0061142 | A1 | 5/2002 | Hiramatsu |
| 2002/0099295 | A1 | 7/2002 | Gil et al. |
| 2002/0154300 | A1* | 10/2002 | Mansfield et al. ............. 356/300 |
| 2002/0177894 | A1* | 11/2002 | Acosta et al. ................. 623/1.24 |
| 2003/0139667 | A1 | 7/2003 | Hewko et al. |
| 2004/0111030 | A1 | 6/2004 | Zeman |
| 2004/0119020 | A1 | 6/2004 | Bodkin et al. |
| 2004/0204651 | A1 | 10/2004 | Freeman et al. |
| 2004/0209237 | A1 | 10/2004 | Flewelling et al. |
| 2004/0220477 | A1 | 11/2004 | Freeman et al. |
| 2005/0049467 | A1* | 3/2005 | Stamatas et al. ............... 600/315 |
| 2006/0241495 | A1 | 10/2006 | Kurtz |
| 2006/0247514 | A1 | 11/2006 | Panasyuk et al. |
| 2007/0024946 | A1 | 2/2007 | Panasyuk et al. |
| 2007/0038042 | A1 | 2/2007 | Freeman et al. |

OTHER PUBLICATIONS

Afromowitz et al., "Multispectral imaging of burn wounds: a new clinical instrument for evaluating burn depth." IEEE Trans Biomed Eng 1988; 35(10):842-50.

Armstrong et al., "Predicting neuropathic ulceration with infrared dermal thermometry." J Am Podiatr Med Assoc 1997; 87(7):336-7.

Beckert et al., "The Impact of the Micro-Lightguide O2C for the Quantification of Tissue Ischemia in Diabetic Foot Ulcers." Diabetes Care 2004; 27(12):2863-2867.

Brearley et al., "Peripheral pulse palpation: an unreliable physical sign." Ann R Coll Surg Engl. May 1992; 74(3):169-71.

Caputo et al., "Assessment and management of foot disease in patients with diabetes." N Engl J Med 1994; 331 (13):85460.

Carlson et al., "A historical overview and update on pulse oximetry." Anesthesiol Rev 1993; 20:173-181.

Cavanagh et al., "Correlates of structure and function in neuropathic diabetic feet." Diabetologia 1991; 34(Suppl 2):A39 (abstract).

Colarusso et al., "Infrared spectroscopic imaging: from planetary to cellular systems." Appl Spectrosc 1998; 52:106A-120A.

Dahab, G. et al, "Digital Quantification of Fibrosis in Liver Biopsy Sections: Description of a New Method by Photoshop Software", Journal of Gastroenterology and Hepatology 19:pp. 78-85, 2004.

Dinh et al. "The use of medical hyperspectral technology to evaluate microcirculatory changes in diabetic foot ulcers and predict clinical outcomes." 2007, Diabetes Care;30:903-910.

Dinh et al. "The use of Medical HyperSpectral Imaging (MHSI) to identify patients at risk for developing diabetic foot ulcers." Diabetes 2005;54(SI):A270.

Ferrara et al. "Clinical applications of angiogenic growth factors and their inhibitors". Dec. 1999. Nature Medicine. vol. 5, No. 12: 1359-1364.

Freeman et al., "Medical hyperspectral imaging (MHSI) of 1,2-dimethylbenz(a)-anthracene (DMBA)-induced breast tumors in rats." Poster #1001. In: 27th Annual San Antonio Breast Cancer Symposium; 2004; San Antonio, Texas: Breast Cancer Research and Treatment; 2004. p. S51.

Frykberg et al. "Diabetic foot disorders: a clinical practice guideline. American College of Foot and Ankle Surgeons." J Foot Ankle Surg 2000;39(5 Suppl):SI-60.

Frykberg et al., "Role of neuropathy and high foot pressures in diabetic foot ulceration." Diabetes Care. Oct. 1998;21(10):1714-9.

Frykberg RG. "Diabetic foot ulcers: pathogenesis and management." Am Fam Physician 2002; 66(9): 1655-62.

Gillies et al., "Systemic effects of shock and resuscitation monitored by visible hyper spectral imaging." Diabetes Technol Therapeut 2003; 5(5):847-855.

Greenman et al., "Early changes in the skin microcirculation and muscle metabolism of the diabetic foot." Lancet 2005; 366: 1711-1718.

Harrington et al., "A cost analysis of diabetic lower-extremity ulcers." Diabetes Care 2000; 23(9):1333-8.

Hittel and Donnelly, "Treating peripheral arterial disease in patients with diabetes." Diabetes Obes Metab 2002; 4 Suppl 2:S26-31.

Johnson, William R., et al., Snapshot Hyperspectral Imaging in Ophthalmology, Journal of Biomedical Optics 12(1), 014036 (Jan./Feb. 2007).

Khan and Newton, "Laser Doppler imaging in the investigation of lower limb wounds." Int J Low Extrem Wounds 2003;2(2):74-86.

Lavery and Gazewood, "Assessing the feet of patients with diabetes." J Fam Pract 2000;49(11 Suppl):S9-16.

Lavery et al., "Practical criteria for screening patients at high risk for diabetic foot ulceration." Arch Intern Med 1998;158(2):157-62.

Martinez, Luis. "A Non-invasive spectral reflectance method for mapping blood oxygen saturation in wounds". Proceedings of the 31st Applied Imagery Pattern Recognition Workshop 2002; p. 1112.

McMillan DE. "Development of vascular complications in diabetes." Vasc Med 1997; 2(2):132-42.

Novo S. "Classification, epidemiology, risk factors, and natural history of peripheral arterial disease." Diabetes Obes Metab 2002; 4 Suppl 2:S1-6.

Palumbo et al., "Peripheral vascular disease and diabetes." In: Harris et al. (editors). *Diabetes in America*, 1st ed, Washington, DC: US Government Printing Office; 1985.

Payette et al., "Noninvasive diagnostics: predicting flap viability with near-IR spectroscopy and imaging." Am Clinical Laboratory 1999; 18:4-6.

Pecoraro et al, "Pathways to diabetic limb amputation. Basis for prevention." Diabetes Care 1990; 13(5):513-21.

Rajbhandari et al., Early identification of diabetic foot ulcers that may require intervention using the micro lightguide spectrophotometer. Diabetes Care 1999;22(8): 1292-1295.

Ramsey et al. "Incidence, outcomes, and cost of foot ulcers in patients with diabetes." Diabetes Care 1999; 22(3):382-7.

(56) References Cited

OTHER PUBLICATIONS

Reiber et al., "Lower extremity foot ulcers and amputations in diabetes." In: Harris et al. (editors). *Diabetes in America.* 2nd ed. Washington, DC: US Government Printing Office; 1995. p. 402-428.

Riaza et al., "Spectral mapping of rock weathering degrees on granite using hyper spectral DAIS 7915 Spectrometer Data." Internl J Applied Earth Observation and Geoinformation Special issue; Applications of imaging spectroscopy 2001;3-4:345-354.

Sheffield et al., "Laser Doppler Flowmetry." In: *Wound Care Practice*. Flagstaff, AZ. Best Publishing Company; 2004, p. 137.

Sowa et al., "Near infrared spectroscopic assessment of hemodynamic changes in the early post-burn period." Burns 2001;27:241-249.

Sumpio BE. "Foot ulcers." N Engl J Med. Sep. 14, 2000;343(11):787-93.

Sykes and Godsey, "Vascular evaluation of the problem diabetic foot." Clin Podiatr Med Surg 1998; 15(1):49-83.

Thenkabail et al., "Hyperspectral vegetation indices and their relationships with agricultural crop characteristics." Remote Sens Environ 2000;71 (Remote Sens Environ): 158-182.

Treado et al., "Infrared and Raman spectroscopic imaging." Appl Spectrosc Rev 1994;29: 1-38.

van der Laak et al, "Hue-Saturation-Density (HSD) Model for Stain Recognition in Digital imagines from Transmitted Light Spectroscopy" Cytometry 39:pp. 275-284, 2000.

Veves et al. "The Use of Medical HyperSpectral Imaging (MHSI) to evaluate microcirculatory changes and predict clinical outcomes: application to diabetic foot ulcers." Society of Vascular Medicine and Biology 17th Annual Scientific Session 2006 (abstract).

Wardlaw et al., "Imaging appearance of the symptomatic perforating artery in patients with lacunar infarction: occlusion or other vascular pathology?", Ann Neurol 2001;50(2):208-15.

Young et al., "The prediction of diabetic neuropathic foot ulceration using vibration perception thresholds. A prospective study." Diabetes Care 1994; 17(6):557-60.

Zamboni et al. "Evaluation of hyperbaric oxygen for diabetic wounds: a prospective study", Undersea Hyper Med 1997; 24(3):175-179.

Zimny et al., "Early detection of microcirculatory impairment in diabetic patients with foot at risk." Diabetes Care 2001; 24(10): 1810-4.

Zuzak et al. "Noninvasive determination of spatially resolved and time-resolved tissue perfusion in humans during nitric oxide inhibition and inhalation by use of a visible-reflectance hyper spectral imaging technique." Circulation 2001; 104:2905-2910.

\* cited by examiner

HYPERSPECTRAL TECHNOLOGY FOR ASSESSING AND TREATING DIABETIC FOOT AND TISSUE DISEASE

REFERENCE TO RELATED APPLICATIONS

The present application claims priority to U.S. Provisional Application 60/709,422 filed Aug. 19, 2005, entitled Hyperspectral Imaging for Assessing Imaging for Assessing and Treating Diabetic Foot Disease, which is hereby incorporated by reference, and is a continuation-in-part of U.S. Non-provisional patent application Ser. No. 11/396,941 entitled Hyperspectral Imaging in Diabetes and Peripheral Vascular Disease, filed Apr. 4, 2006, which is hereby incorporated by reference, which claims priority to U.S. Provisional Patent Application Ser. No. 60/667,677 entitled Hyperspectral Imaging in Diabetes, filed Apr. 4, 2005 and to U.S. Provisional Patent Application Ser. No. 60/785,977, filed Mar. 27, 2006 and entitled Hyperspectral Imaging of Angiogenesis.

BACKGROUND OF THE INVENTION

1. Field of the Invention

This invention relates generally to the evaluation and care of the extremities and tissues of persons affected by the disease diabetes or other ailments or injuries that may affect the ability to perfuse, oxygenate or heal tissue, particularly to the measurement of changes in tissue oxygenation by natural pressures applied to the foot or other tissues of the body that may lead to ulceration or tissue injury and using this information to offload pressure or provide treatment of injured areas or in areas at high risk and thereby treat or prevent ulceration or other tissue damage.

The present invention is directed to apparati and methods for assessing tissue oxygenation, hydration, oxygen delivery and/or oxygen extraction with hyperspectral imaging and, in particular, tissue oxygenation associated with the foot and other tissues.

2. Description of the Background

Diabetes (or diabetes mellitus) is a chronic disease that affects up to 6% of the US population. When diabetes is present, either the body produces less or no insulin, and/or does not properly use insulin. Insulin is a hormone necessary to maintain blood sugar concentration at normal levels. When insulin is not produced or used correctly by the body, glucose remains in the bloodstream instead of being shuttled into cells for energy production, resulting in high blood glucose, or high "blood sugar" levels.

High blood sugar can manifest its presence through multiple symptoms, including thirst, frequent urination, weight loss, increased hunger, blurred vision, irritability, tingling or numbness in the hands or feet, frequent skin, bladder, or gum infection, wounds that do not heal, and extreme, unexplained fatigue.

If left untreated, diabetes can lead to death, and even diabetics undergoing doctor-supervised treatment suffer an increased death rate compared to the average population. Diabetes is also associated with progressive disease of the microvasculature. Diabetics also face risk of multiple complications during their lifetime arising from the disease. Some of the more serious complications include: heart disease (the leading cause of death in diabetics); stroke (risk of stroke is 2 to 4 times greater for diabetics); high blood pressure (about 73% of diabetics); blindness (diabetic retinopathy causes 12,000 to 24,000 new cases each year and diabetes is the leading cause of new cases of blindness among adults 20-74 years old); kidney disease (diabetes is the leading cause of treated end stage renal disease, accounting for 43% of new cases); nervous system disease (60-70% of diabetics have mild to severe damage, such as impaired sensation of pain in the feet or hands, slowed digestion, and carpal tunnel syndrome); dental disease (almost one-third of diabetics have severe periodontal diseases); pregnancy complications (poorly controlled diabetes before conception and during the first trimester of pregnancy can cause major birth defects in 5-10% of pregnancies and spontaneous abortions in 15-20% of pregnancies); and amputations (more than 60% of non-traumatic lower-limb amputations in the United States occur among diabetics).

Studies of all patients with diabetes under primary care have delivered annual rates of ulcer formation of 5-6%. (Recently reported VA study with an overall annual rate of 6.1% in all patients 40 yrs).[1] Stratification into higher risk groups delivers an annual de-novo ulcer formation rate of 33% in patients with a history of amputation, 19% in neuropathic patients with bony deformity and no history of ulcer or amputation and 11% in neuropathic patients with no history of ulcer or amputation.[2,3]

Diabetic neuropathic foot disease is the most common cause of amputation in the United States and arises as a sequella of several of the complications listed above. These complications often stem from the disturbance of the body's metabolism caused by the prolonged high blood sugar. The disturbance includes increased levels of serum cholesterol, triglycerides, and glucosylated hemoglobin, which lead to precipitation of the substances along the small blood vessels (especially capillaries) everywhere in the body, and more so in terminal blood vessels, like those found in the legs and feet. This then leads to damage to or stenosis of the blood vessels, ultimately resulting in a condition termed diabetic microangiopathy, or literally, disease of the capillaries related to diabetes. Longstanding microvascular disease that is widespread may decrease the total capacity of blood circulation within the body, which both directly and indirectly through kidney damage contributes to the high blood pressure condition referenced above. The most dangerous effect of microvascular disease, is occurrence of ischemia (decreased blood supply). This is often manifest in symptoms in the foot and leg, although all tissues may suffer ischemic effects from microvascular disease. This condition can progress with inadequate supply of oxygen and nutrients, eventually producing devitalization and change of texture and color of the foot, often starting with a toe or portion of the forefoot, which can then spread to the rest of the limb. This can take the form of tissue ischemia or frank gangrene.

Diabetic patients also have increased risk of complications associated with their lower extremities, especially the feet, due to nervous system disease, as described above, that can lead to a partial or complete loss of feeling. A healthy person that starts to feel pain when subjected to continuous local pressure may shift their body or make other suitable alterations to automatically lessen the discomfort; however, patients having a sensory loss are deprived of this protection and are therefore common victims of pressure sores and open wounds that can become ulcerated. They also tend to balance themselves differently which can cause progressive alteration in the bony structure of the foot. It is therefore desirable to detect the pressure points or locations of shear stress in the foot to prevent pressure sores and wounds so that a patient who might not be able to recognize existence of a pressure point inducing condition can take curative or preventative measures to eliminate or reduce the condition. More important to just detecting pressure points is to combine this information with the presence of vascular compromise which is the result of a decrease in tissue oxygenation that can be due to a combination of microangiopathy or other influences on adequacy of systemic perfusion to the tissue, large vessel disease due to macrovascular atherosclerosis or obstruction and local factors due to inflammation to an extremity as measured by local tissue oxygenation.

The development of protocols capable of diagnosing potential areas for the development of plantar ulcers would be of great value in decreasing and preventing diabetic foot amputation. Similarly, protocols directed at diagnosing other areas of potential ulceration in diabetic and non-diabetic people, such as sacral ulcers, ulcers on amputation stumps or foot ulcers in athletes would be useful. Special utility would occur in patients with diseases or therapeutic circumstances in which the skin may become fragile such as with scleroderma or other collagen vascular diseases or treatment with steroids.

Diabetic foot lesions are an underlying cause of hospitalization, disability, morbidity, and mortality, especially among elderly people. A protocol for early detection of plantar ulceration would avoid the need for follow-up examinations, supplementary examinations, local wound debridement, orthopedic appliances, and in some critical cases frequent hospitalization, and amputation. Estimates have shown that between 2-6% of diabetic patients will develop a foot ulcer every year,[4, 5] and that the attributable cost for an adult male between 40 and 65 years of age is more than $27,000 in 1995 US dollars for the two years after diagnosis of the foot ulcer.[4]

Devices are known for indicating to persons having diminished sensation in the foot that their feet are being exposed to excessive stress conditions that could possibly lead to plantar ulcers or worse. Many of these devices include shoes, which detect excess pressure through a force sensor and signal the wearer of the existence that a threshold pressure has been reached. Examples of such devices are described in U.S. Pat. No. 5,566,479, U.S. Pat. No. 4,610,253, U.S. Pat. No. 4,647,918, U.S. Pat. No. 5,642,096, and U.S. Pat. No. 6,918,883 B2.

Diabetes is a chronic, life-threatening disease for which there is no known cure. It is the fourth leading cause of death in the United States. Over 21 million people in the United States have diabetes and more than 1,000,000 new cases are diagnosed each year. It is estimated that there are at least 194 million people with diabetes worldwide. Type I (or juvenile) diabetes, the most severe form of the disease, comprises 5-10% of diabetes cases and requires daily treatment with insulin to sustain life.

Although medical research experts have not yet found a cure, they have discovered that they can minimize the ravages of diabetes related complications by delineating specific risks, accurately assessing evolving pathologies, and ensuring the rapid institution of effective therapy. This is particularly true in providing appropriate care for the diabetic foot.

The development of an ulcer in the diabetic foot is commonly a result of a break in the barrier between the dermis of the skin and the subcutaneous fat that cushions the foot during ambulation. This rupture can lead to increased pressure on the dermis, resulting in tissue ischemia and eventual death, ultimately manifest in the form of an ulcer.[6]

There are a number of factors that weigh heavily in the process of ulceration.[7] These factors, such as neuropathy, microcirculatory changes, peripheral vascular disease, obesity and musculoskeletal abnormalities, affect different aspects of the foot, leading to a synergy of effects that greatly increase the risk of ulceration.[8]

Neuropathy results in a loss of protective sensation in the foot, exposing patients to undue, sudden or repetitive stress. It can lead to atrophy of the small intrinsic muscles, collapse of the arch, and loss of stability in the metatarsal-phalangeal joints. Neuropathy leads to lack of awareness of damage to the foot as it may be occurring, physical defects and deformities[9] which lead to greater physical stresses on the foot. In addition, it can lead to increased risk of cracking and the development of fissures in calluses (a potential entry for bacteria and increased risk of infection).[10]

Microcirculatory changes are seen in people with in association with hyperglycemic damage.[11] Functional abnormalities occur at several levels. Hyaline basement membrane thickening and capillary leakage may impair diffusion of nutrients. When comparing the microcirculation of the forearm and foot in diabetic patients with and without neuropathy, the endothelium-dependent and endothelium-independent cutaneous vasodilation is lower in the foot.[12] On a histologic level, it is well known that diabetes causes a thickening of the endothelial basement membrane which in turn may lead to impaired endothelial cell function.

Peripheral vascular disease (PVD) is "macrovascular disease" caused by atherosclerotic obstruction of large vessels resulting in arterial insufficiency.[13] It is more common and more severe in diabetics.[14] Like non-diabetics, people with diabetes may develop atherosclerotic disease of large-sized and medium-sized arteries, such as aortoiliac and femoropopliteal atherosclerosis. However, significant atherosclerotic disease of the infrapopliteal segments is particularly common in the diabetic population. The reason for the prevalence of this form of arterial disease in diabetic persons is thought to result from a number of metabolic abnormalities, including high LDL and VLDL levels, elevated plasma von Willebrand factor, inhibition of prostacyclin synthesis, elevated plasma fibrinogen levels, and increased platelet adhesiveness.

Musculoskeletal abnormalities (altered foot mechanics, limited joint mobility, bony deformities) can lead to harmful changes in biomechanics and gait, increasing the pressures associated with various regions of the foot. Alteration or atrophy of fat pads in the foot from increased pressure can lead to skin loss or callus, both of which increase the risk of ulceration by two orders of magnitude.

People with diabetes are more likely to express a combination of the aforementioned factors than non-diabetics, leading the far greater incidence of diabetic foot ulcers in type 1 and type 2 diabetes compared to similar nondiabetics. Clearly, however, foot ulcers can occur in non-diabetics, especially ischemic ulcers seen in patients with peripheral vascular disease and associated with atherosclerosis, hypertension and a history of smoking.

A lower extremity ulcer develops in about 15% of patients with diabetes during their lifetime. Foot pathology associated with vascular disease is a major source of morbidity among diabetics and a leading cause of hospitalization. The infected and/or ischemic diabetic foot ulcer accounts for about 25% of all hospital days among patients with diabetes. Costs of foot disorder diagnosis and management are estimated at over $2 billion annually. Foot ulceration precedes 85% of lower extremity amputations. Proper prevention, evaluation and treatment of diabetic foot disease would clearly improve the quality of life for people with diabetes.

The current market for the diabetes device industry is over $4 billion dollars, and growing 18% annually. This has been primarily in the glucose self-testing area, but demonstrates the large dollars spent annually by patients and the health care system (Medicare and over 60% of other insurers now cover the costs of these devices and supplies.) to take the preventative steps of maintaining better glycemic control to minimize diabetic complications. This demonstrates the huge and growing scope of the overall diabetes market and that this defines the basis of a receptive community of patients and caregivers that will embrace innovative technologies to combat the complications of type 1 and type 2 diabetes such as diabetic foot ulcer.

There is a huge unmet need in prevention, accurate diagnosis and monitoring of therapeutics in diabetic foot disease. Currently the monitoring of pharmacologic therapy is grossly insufficient. Hyperspectral technology will be useful in both drug development and in evaluating clinical progress under a specific pharmacologic therapy. Surgical decision-making will be improved and necessary medical and surgical interventions can be better timed. This will provide huge savings to the health care system. Appropriate pairings of hyperspectral measurements (to deliver a quantitative diagnostic) with therapeutics (both pharmaceuticals and devices) provide diagnostic/therapeutic pairings which can both help the physician select and monitor therapy.

Current solutions are ineffective or incomplete. Diabetic feet are at risk for a wide range of pathologies including infection, ulceration, deep tissue destruction, and/or metabolic complications. Cumulative risks for ulceration include neuropathy, foot-ankle deformity, high planar pressure, poor glucose control, and previous ulceration. Noninvasive techniques now employed in screening for vascular related foot disease have not proven useful in predicting or preventing disease. There is currently no method to assess accurately, rapidly, and noninvasively the predisposition to serious foot complications, to define the real extent of disease or to track the efficacy of therapeutics over time.

Diabetic vascular disease was once thought to involve only the microvasculature. This belief has since been dispelled at both the histologic and surgical levels. It is now possible to perform pedal bypass on the ischemic diabetic leg with improved limb salvage rate and reduction in amputation rates. Although it is possible to have adequate inflow and outflow to the diabetic foot, the microvasculature of the diabetic foot is physiologically altered in terms of flow regulation such that tissue loss can continue to occur.

Functional abnormalities in the microcirculation occur at several levels. Hyaline basement membrane thickening and capillary leakage may impair diffusion of nutrients. When comparing the microcirculation of the forearm and foot in diabetic patients with and without neuropathy, the endothelium-dependent and endothelium-independent cutaneous vasodilatation is lower in the foot.[12] On a histologic level, it is well known that diabetes causes a thickening of the endothelial basement membrane which in turn may lead to impaired function of the endothelial cell. Nitric oxide is produced within the endothelial cell and functions to relax smooth muscle cells leading to dilation of the blood vessel. Diabetes, through several molecular mechanisms, functions to decrease the amount of available nitric oxide and thus reduces vasodilatation. The loss of vasodilatation is then thought to lead to early nerve dysfunction through ischemia and nutrient deprivation.[15] As neuropathy worsens, the nociceptive C fibers are impaired leading to a loss of the ability to mount a hyperemic response to inflammation.[16] This places the foot at risk in terms of infection and the ability to heal minor wounds. Successful revascularization has shown to improve the microcirculation of the skin, but does not completely alter the vasoreactivity or the nociceptive C fiber response.[17] This places the revascularized patient still at risk for slow healing of ulcers and infection which may further compromise the foot in spite of adequate inflow.

Although not every diabetic foot disorder can be prevented, it may be possible to effect dramatic reductions in their incidence and morbidity through appropriate prevention and management tools.

Currently available tools for monitoring plantar pressures include pressure sensitive mats (RSscan Labs, UK) and thin in shoe pressure sensitive plates (Tekscan, Boston, Mass.). Other tools are available to measure the contour of the foot including plastic casts and NIR surface scanners (PedAlign, San Diego, Calif.). Specially tailored orthotics are then constructed from information gathered from these measurements that either offload pressure or evenly distribute pressure to the sole of the foot.

A study was recently performed using interferometry for detecting plantar pressure distribution involving a laser light oriented towards a compressed plate.[18] This approach involves a pressure plate, which compresses when subjected to a load. The interferogram produced represents the pattern of pressure distribution across the plate. Such approaches as this pose an improvement over the cumbersome, expensive footwear noted above, but this method still suffers from drawbacks, such as ease of use, mass availability, and expense. Further, such methods are only useful for analyzing the bottom or sole of the foot and fails to account for pressure points or locations of shear stress on other parts of the foot. These other methods also do not take into account generalized (systemic), regional or local influences which may decrease perfusion or oxygenation to a given region of the foot.

The effectiveness of these systems to reducing foot ulcerations is still unanswered beyond anecdotal evidence, with groups squaring off between measuring pressure or contour as the important endpoint. It has not been known to measure the spatial distribution of local tissue oxygenation, perfusion oxygen delivery or oxygen extraction while under pressure.

Peripheral Vascular Disease and "Islands of Ischemia"

Another form of ulcer is arterial or ischemic ulcer. These occur in patients with peripheral arterial disease, with or without diabetes. Over 12 million Americans have peripheral arterial disease and the incidence is rising. Ischemic ulcers arise from a lack of perfusion to the tissues adequate to meet the demands of maintaining tissue integrity or of healing a minor injury. The lack of perfusion can be due to blockage of a major vessel, smaller vessels or due to microcirculatory disease. Treatment often requires arterial vascular bypass if this is anatomically feasible. Because of the decrease in perfusion in these ulcers, compression or pressure of any kind is contraindicated.

By reducing flow to the foot, peripheral arterial disease can impede healing; reducing the supply of oxygen and nutrients that tissue requires to maintain the repair process and the viability of the dermal barrier, and significantly amplify the problems associated with diabetic microvascular and neuropathic disease. Each year 343,000 peripheral angiograms, 100,000 peripheral bypasses performed for limb salvage and 135,000 amputations are performed. 82,000 of these amputations are on type 1 and type 2 diabetics. Symptoms and current diagnostic tests are not very sensitive indicators of disease progression or response to pharmacologic therapy.

Rhodes et al. coined the phrase "islands of ischemia" after observing non-healing foot ulcers in diabetic patients despite adequate peripheral bypass.[19] In one experiment, a total of fourteen patients were evaluated using Doppler, pulse volume recordings (PVR), and transcutaneous oxygen tensions (TcPO2) in diabetic patients following distal bypass. Group I consisted of eleven patients with no evidence of ulcer following bypass, while Group II consisted of three patients with persistent ulcers despite revascularization. The two groups were compared based on their PVR and TcPO2 results. Both groups were shown to have statistically significant increases in both PVR class and foot TcPO2 ($p<0.001$). However, despite overall increases in foot TcPO2, the non-healing ulcer group was found to have TcPO2 values less than 20 mm Hg adjacent to the areas of ulceration. This suggests that despite adequate inflow to the extremity with peripheral bypass, "islands of ischemia" exist where inadequate perfusion occurs, thus making the area more susceptible to ulcer formation and inability to heal an ulcer. The etiology of "islands of ischemia" is considered multifactorial and involves abnormal microvascular regulatory mechanisms, histologic changes, and altered neurophysiology.

Venous and Mixed Ulcers

In addition to the diabetic and ischemic ulcers described above, ulcers can also occur primarily associated with venous disease in patients with or without diabetes. About 70% of all leg ulcers are venous ulcers. Venous leg ulcer occurs secondary to underlying venous disease whereby blockage or valve damage leading to valvar insufficiency of the superficial, deep or perforating veins leads to venous hypertension. The ulcer usually presents within the region of the leg just above the ankle. In general, venous ulcers are treated with compression stockings, wraps or bandages. Graduated compression can reduce the elevated pressures in the superficial veins. Compression may also improve the competence of the valves.

Mixed ulcers occur when there is both venous and arterial insufficiency. Generally these present as venous ulcers in someone with some degree of arterial insufficiency. In this circumstance, arterial vascular bypass may also be required. If this is not possible, careful use of compression may be undertaken to help decrease the venous pressure without compromising arterial flow, but this can be difficult to accomplish. Understanding the adequacy of tissue perfusion and oxygenation before undertaking compression therapy is important as is monitoring this during therapy.

Decubitus Ulcers

Sacral and other decubitus ulcers and other forms of pressure sores represent other examples of tissue damage that are to date unable to be prevented or treated in an optimized fashion. They also lead to loss of quality of life, loss of life itself and also represent a huge burden to the health care system. Such ulcers occur in debilitated, hospitalized, paralyzed, malnourished patient groups and in other situations in which pressure is placed on a region of tissue that in some way compromises its viability.

There are also other situations in which abnormalities of skin, vasculature or collagen lead to tissue fragility. This can be associated with a variety of circumstances including malnutrition, cancer, catabolic state, debilitation, steroid use, collagen vascular diseases, and advanced age.

Limp Amputation

Limb amputation is a significant problem due to a variety of causes including trauma, diabetic disease and atherosclerosis. The prevalence of amputation in the United States is approximately 1 million,[20] and over 43,000 new major amputations are performed yearly[21]. The amputee is not only challenged by having the underlying disease or cause of amputation to deal with but also having to learn to use the artificial limb and be beleaguered by the attendant complications that may arise from poor prosthetic fit. This may include recurrent residual limb breakdown predisposing the patient to pain, stump or tissue ulceration or breakdown, osteomyelitis, and sepsis as well as abnormal gait which can occur with improper fit with a secondary result in safety concern, an increase in the energy cost of ambulation and the predisposition to developing osteoarthritis. To date, the evaluation of prosthetic fitting and the addressing of residual limb complications is largely based on limited objective criteria, symptoms and complaints of the amputee and a rather subjective examination of the residual limb, prosthesis, and gait pattern. The implementation of an improved method of assessment of the design of prosthetics would be an advantage which would encompass both pressure and perfusion or oxygenation data would be an advantage.

Spectroscopy in Medicine

Spectroscopy, like many other analytical techniques, has undergone an evolution in terms of the types of research fields in which it is being utilized. From its early beginnings, it was, and continues to be, a plentiful research field in the hands of physicists. Later, chemists discovered that spectroscopy was a useful tool for the investigation of complex molecular structures. Later still, biologists discovered the usefulness of spectroscopy in the analysis of the structures of biomolecules.[22]

Over the last decade, spectroscopy has emerged into medicine. The natural progression of spectroscopy into medicine has paralleled another spectroscopic technique, MRI. The original investigations into problems of medical significance were based on the premise that the biochemistry of a tissue must change before changes in anatomy or morphology, the current standard criteria for many diagnoses, become apparent, and that these biochemical changes will be contained within the spectral signature. Therefore, chemical changes of a disease state should be apparent by spectroscopic analyses prior to any clinical appearance. The progress of research thus far has consistently shown this to be a good premise.[22]

Spectra are known to be sensitive to subtle changes in molecular composition and conformation. Spectroscopic analysis of biomolecules is a well established field; and, as any chemist knows, the spectrum of a molecule forms a unique "fingerprint" of that compound. However, this maxim only holds true for pure compounds. Tissues, be they human or animal, are an incredibly complex and highly variable mixture of compounds. The typical spectra obtained from tissue are a weighted average of the spectral features of each of the chemical constituents being sampled within a given sample volume, and as such, these spectra contain information about the biochemical state of the entire sample.

The major obstacle in medical spectroscopy has been sorting out useful diagnostic information from the inter and intra-sample variability. It is not nearly enough to take a spectrum from a healthy piece of tissue and a diseased piece of tissue, compare them, and make valid claims regarding their disease state. It is necessary to take into account the range of disease expressions which occur over a population, as well as the intrinsic variability of tissue spectra during such analysis. This process requires either large, statistically relevant numbers of spectra or a methodology that takes into account the intrinsic inter-sample variability and spatial heterogeneity.

Spectroscopic investigations of medical interest can be roughly divided into three major areas: clinical chemistry, where the goal is to provide a quantitative analysis of blood or other fluid analytes; pathology, which attempts to provide an alternative pathological assessment of a tissue biopsy; and in vivo analyses, where the analysis is done without the need for an invasive procedure. The vision of having a small, inexpensive, portable instrument capable of making a rapid, non-invasive assessment of some relevant medical parameter has provided the driving force behind the application of visible and near-IR spectroscopic techniques to issues of medical interest.

The optical properties of tissue are governed by the bulk scattering properties as well as their absorbance. Variations in tissue or blood analyte composition and/or concentrations will affect visible and near-IR tissue absorbance, while changes in the tissue blood-volume will affect the scattering properties. The interpretation of in-vivo reflectance data is further complicated in that most physical situations which modify tissue absorbance also affect tissue scattering. Visible and near-IR spectroscopic methods have been used for decades in operating theatres in the form of pulse oximeters. These simple systems utilize the different oxyhemoglobin and deoxyhemoglobin absorption bands to determine arterial oxygen saturation.

Skin Spectroscopy

A small portion of visible light shining on the skin of the foot is reflected off the surface. Most of the light passes into the skin through the stratum corneum (~25 μm thick on the dorsal surface and considerably thicker on the plantar surface of the foot), the epidermis (~100 μm thick) and into the dermis. The structural features of the dermis (collagen and elastin fibrils, arterial and venous plexus) backscatter the light. This backscattered or re-emitted light maintains the same wavelength spectrum as the incident light, but the intensity is modified by the absorption of skin chromophores.[22-25] The intensity modification is directly related to the concentration of chromophores present in the volume of skin investigated. The log of the ratio of the re-emitted to the incident light intensity yields an absorption spectrum of the chromophores.

The primary absorbing chromophores in skin are oxyhemoglobin (oxyHb) and deoxyhemoglobin (deoxyHb) (present in the dermis), hemoglobin breakdown products such as bilirubin and methemoglobin, and melanin (present in the epidermis). The spectral properties have been reported.[26-28] Hemoglobin has distinct spectral signatures, depending on whether it is oxyHb or deoxyHb. The in-vivo absorption spectra of these compounds have been well-characterized.[29] When compared to standard in-vivo absorption spectra, information about the type and also the relative concentration of chromophores in the region of investigation may be quantified.[30, 31]

Single point diffuse reflectance (DR) spectroscopy has been used in a variety of studies to investigate the response of the in vivo microvasculature to stimulation. The ratio oxyHb to deoxyHb has been used to derive the oxygen extraction by the tissue, which occurs with metabolism. DR has been used to study oxygen saturation modulation in a variety of tissues and physiologic and pathologic conditions such as pancreatic microcirculation,[32] irritant-induced inflammation,[33] ischemia-reperfusion injury[34] and effect of UV irradiation,[35] skin blanch tests.[36] Work by Mansfield et al. has shown the utility of DR spectroscopy in the non-subjective diagnosis and monitoring of rheumatoid arthritis[37] and basal cell carcinoma.[38]

Point spectroscopy of the skin has been shown to be useful for some applications. The understanding derived from previous spectroscopic studies of complex biological systems is essential to accurate design of HT experiments as well as for optimizing the interpretation of imaging data. Understanding the spectroscopic properties of the human body and the physiology of the skin are prerequisites to interpreting HT results.

Hyperspectral Technology

HT or hyperspectral imaging is a method of "imaging" spectroscopy" that generates a "gradient map" of a region of interest based on local chemical compositions. HT has been used in a wide variety of applications ranging from geological and agricultural to military and industrial, the major airborne applications are in mineral exploration, environmental monitoring and military surveillance.[39-42] HT has recently begun to be applied to medicine.[43-45] HT for medical applications has been shown to accurately predict viability and survival of tissue deprived of adequate perfusion, and to differentiate diseased (e.g. tumor) and ischemic tissue from normal tissue.

In medicine, spectroscopy is used to monitor metabolic status in a variety of tissues; consider the spectroscopic methods used in pulse oximeters which utilize the different absorption bands oxy- & deoxy-Hb to estimate arterial oxygen saturation. No other method however provides information towards the spatial distribution or heterogeneity of the data. Such spatial information is achieved by HT, where the multidimensional (spatial & spectral) data is represented in what is called a "hypercube" (see example in FIG. 2). The spectrum of reflected light is acquired for each pixel in a quadrant and each such spectrum is subjected to standard analysis. From this we create a map of the tissue based on the chemistry of the region of interest.

Tissues have optical signatures that reflect their chemical characteristics, can these can be measured using diffuse reflectance (DR) techniques with an optical probe placed at the site. Tissues have two major optical chromophores of physiological relevance in the visible light spectrum: oxyhemoglobin (OxyHb) and deoxyhemoglobin (DeoxyHb). When measured by hyperspectral technology, these chromophores delineate local oxygen delivery and extraction within the tissue microvasculature. With ischemia, such as in cases of limb ischemia or shock, the spatial composition of OxyHb and DeoxyHb varies across the skin, presenting a mottled appearance. This explains the variability and unreliability seen in tissue oximetry when measured at a single site. Tissue undergoing wound healing also presents varying oxygenation status depending on where the probe is placed relative to the wound. This makes point measurements poor indicators of the wound healing process HT enables the efficient collection of data from over a million points, producing a 2-dimensional map of the state of tissue oxygenation including its spatial variation and thus provides an assessment of "oxygen anatomy."

Tissue oxygenation mapping is a compelling application of HT. Single point DR spectroscopy has been used to study oxygen saturation in a variety of tissues and physiologic and pathologic conditions such as localized microcirculation, irritant-induced inflammation, ischemia-reperfusion injury, effect of UV irradiation, optical detection of cancer, and peripheral arterial disease. A drawback of single point DR is that it provides no spatial information of tissue oxygenation and for complex systems it is clearly desirable to collect spatial information to monitor local variations, as different regions within the tissue may experience vastly different levels of blood flow, perfusion, and oxygen extraction. This is highly important when assessing either regional blood flow or the area around a wound. Systemic microvascular status, regional blood flow patterns and local physiology all play a role.

Hyperspectral imaging combines the chemical specificity of spectroscopy with the spatial resolution of imaging. In HT light is separated into hundreds of wavelengths using any of a number of possible spectral separators and collected on a charge-coupled device (CCD) in much the same way that a picture is taken by an ordinary camera. In other embodiments, CMOS could be used instead of CCD, or some similar type of sensor. A spectrum of penetrated and reflected light is acquired for each pixel in a region, and each such spectrum can be subjected to standard analysis. This allows the creation of an image representing the chemistry of the region of interest.[46]

Hyperspectral Technology (HT), in one guise or another, has become a useful tool for the investigation of spatial heterogeneity in spectral properties in a variety of fields of study ranging from astronomy to medicine. Used for decades in airplane and satellite mounted systems for the mapping of land use and soil types, it has moved in the last five years into a large number of application areas.[39-41] Of particular interest here is the use of HT in the fields of biophysics and medicine. The combination of spectroscopic imaging and microscopy has proved very useful in the investigation of the spectral properties of slices of tissue.[42, 43] In addition to being useful for the investigation of microscopic structures, HT systems for imaging macroscopic structures have been shown to be useful in the monitoring of the spatial distribution of skin oxygenation.[44, 45] HT, however, allows mapping of the regional variations in hemodynamic parameters in response to tissue perfusion.

Changes in the absolute or relative amounts of oxyhemoglobin and deoxyhemoglobin can be measured. Additionally, determining the hemoglobin oxygen saturation (the ratio of oxyhemoglobin divided by the sum of oxyhemoglobin and deoxyhemoglobin) and the total hemoglobin (oxyhemoglobin plus deoxyhemoglobin) is relatively easy given the differing spectra of these two moieties. Unlike single point spectroscopy,[23] hyperspectral technology (HT) allows mapping of regional variations in hemodynamic parameters in response to tissue perfusion. Unlike infrared thermography, HT does not map the thermal emission of the tissues. Instead, it relies on the hemoglobin oxygen saturation and other biomarkers of that tissue. One application of HT is in the determination of tissue viability following plastic surgery.[47] Tissue which has insufficient oxygenation to remain viable is readily apparent from oxygen saturation maps calculated from near-IR spectral images acquired immediately following surgery; clinical signs of the loss of viability do not become apparent for 6 to 12 hours post-surgery.[48]

HT has been studied in a hemorrhagic shock model. An HT system was designed and built for in-vivo use on large animals and human subjects. HT was performed on the ventral surface of the skin in a porcine model. After the image was processed and false colors were applied, light pixels indicated areas of high relative oxygen saturation (O2-sat), whereas dark pixels indicated areas of low O2-sat. It is particularly interesting to note that the mottling seen during hemorrhagic shock features areas of very high tissue oxygenation, alternating with areas of very low tissue oxygenation. The most remarkable finding in these images is the presence of increased regional variability, or "subclinical mottling," during hemorrhagic shock. As in the plastic surgical model, here HT demonstrated and quantified changes that were not visible to the naked eye. These data indicated early alterations in metabolism. As a more sensitive imaging tool, HT is useful to researchers and clinicians interested in understanding the underlying physiology or monitoring the effects of therapy in their patients.[49]

Hyperspectral technology has several features making it a valuable technique for screening and evaluating the foot in diabetes and other peripheral vascular disorders. The technique is noninvasive, rapid, and can be performed during regularly scheduled office visits without the necessity for prior patient preparation. The clinical procedure takes under a minute and requires little more than positioning the patient carefully and taking a pre-programmed series of images at various wavelengths of light with the hyperspectral camera.

Treatment and Prevention of Tissue Breakdown

When tissue breakdown or ulceration is present, therapies are applied to the tissue. In the case of diabetic or ischemic ulcers of the foot, the foot may be offloaded or pressure otherwise relieved from the injured area by bed rest, cut-outs in footwear, total contact casting or other similar treatments. Negative pressure may be applied to assist in healing. In the case of venous ulcers, compression stockings, bandages, wraps or mechanical pumping devices may be applied. Intermittent compression has been used to improve healing of tissue. These therapies have also been applied to prevent tissue breakdown in tissue considered to be at risk for ulceration.

Generally in patients considered to be at risk for diabetic or ischemic ulcer formation, methods are undertaken to evenly distribute pressure to the tissue. In the case of the foot this takes the form of contoured shoe soles, footwear and orthotics and in the case of bed ridden patients air or water beds. However, it is important to understand that in fact to optimize therapy, it should not be uniform pressure that is the goal, but rather applying the least amount of pressure to the areas of tissue most at risk. It would be preferred to identify areas of tissue most at risk and combine this information with contour or pressure mapping data that has been used to apply uniform pressure, to design orthotics or cushions to deliver pressure tailored to the needs of the tissue. In order to prevent diabetic, ischemic, neuropathic or other foot or tissue ulcers patients need more than just uniform pressure relief. Known methods do not solve the mismatch between pressure, perfusion, oxygen delivery and oxygen extraction to meet the demands of the tissue. Foot or other tissue that is poorly perfused or metabolically unstable is more susceptible to the effects of pressure on the region. Therefore, there still remains a need for a method for detecting regions of the foot that are at risk in order to minimize pressure and shear stress especially in regions of poor tissue oxygenation or perfusion.

The applicability of HT in the care of patients with peripheral vascular disease projects into both the clinical setting and operating room. Patients with peripheral vascular disease present with varying degrees of claudication, chronic wounds/ulcers, and gangrene. Non-invasive clinical assessment of these patients is limited. Ankle/brachial indices are limited by both inter- and intra-observer variability. Ultrasound/laser Doppler only reveals flow within a vessel and not degree of perfusion in the tissue. Transcutaneous oxygen tension can only evaluate a single point at a time. HT bridges the gap between the above modalities and allows real time analysis of tissue perfusion in the entire limb. This will allow the vascular surgeon to evaluate the anatomy specifically and determine which areas of the extremity are non-perfused and which are non-viable. This information will be able to help guide surgical and medical therapy. As an emerging technology, HT shows great promise in the evaluation of tissue perfusion.

SUMMARY OF THE INVENTION

Accordingly, one embodiment of the invention is directed to a gradient or index map for directing the treatment of ulceration of diabetic patient feet depicting the level of tissue oxygenation due to pressure from distribution of weight on the surface of the foot measured by hyperspectral technology, laser Doppler imaging, thermal imaging, or an analysis of angiographic, duplex ultrasound or MRA information. Imaging or mapping data is collected while the patient is standing, walking or while seated, supine or prone. Pressure information as measured by pressure mats or force plates and contour information measured through casting or laser surface scanning is used in combination with the HT oxygenation index map or other perfusion information to tailor make insoles or other orthotics to reduce pressure at high risk areas.

Other embodiments and technical advantages of the invention are set forth below and may be apparent from the drawings and the description of the invention which follows, or may be learned from the practice of the invention.

Some embodiments of the invention can be a method of ameliorating a disorder by determining a physiological state of a tissue in response to a physical stress comprising:

determining the physiological state of the tissue, wherein said tissue is not subject to the physical stress, to obtained an unstressed physiological state;

subjecting the tissue to a physical stress;

determining the physiological state of the stressed tissue to obtain a stressed physiological state; and identifying areas of the tissue or corresponding aspects of the physical stress that can be modified to reduce the difference between the stressed and unstressed physiological states.

Further embodiments the method can comprise wherein determining the physiological state of the tissue, wherein said tissue is not subject to the physical stress to obtained an unstressed physiological state is determined from a control database of said physiological states.

In further embodiments the method can comprise comparing the stressed physiological state with the unstressed physiological state to identify areas of the tissue or corresponding aspects of the physical stress that can be modified to reduce the difference between the stressed and unstressed physiological states.

In other embodiments the tissue is a toe, a foot, a leg, a finger, a hand, an arm, or any portion thereof.

In other embodiments the physiological state comprises tissue oxygenation, tissue metabolism or tissue perfusion.

In other embodiments determining the physiological state is made by obtaining a hyperspectral or multispectral image of the tissue.

Some other embodiments the invention can comprise a method for designing a prosthetic device comprising:

generating HT gradient map of the stressed verses the unstressed tissue according to the method of claim 11;

identifying areas of the tissue that are at risk for ulcer formation from said gradient map; and designing the prosthetic devise to reduce pressure to those areas of the tissue identified to be at risk from the gradient map.

In further embodiments, the design reduces the risk of tissue ischemia in unbroken skin, formation of an ulcer or wound, formation of a plantar ulcer, venous stasis, venous ulcer disease or an infection.

Other embodiments of the invention can comprise a method for orthotic treatment for preventing plantar ulcer formation comprising:

generating a hyperspectral image, gradient map of the sole of a foot;

identifying areas of the sole that are at risk for ulcer formation from said gradient map;

redistributing pressure from said areas.

Other embodiments of the invention can comprise a method for orthotic treatment in preventing ulcers on the tissue of a foot or limb stump comprising:

obtaining a HT map of the tissue that combines information about pressure placed by a prosthetic device on the tissue and gravity, and adequacy of tissue oxygenation, tissue metabolism or tissue perfusion of the tissue; and modifying the prosthetic device to maximize tissue oxygenation, tissue metabolism or tissue perfusion of the tissue.

Other embodiments of the invention can comprise an instrument which comprises:

a collector for collecting data on pressure or shear stress of a tissue;

another collector for collecting data on tissue oxygenation or perfusion;

a register for combining both sets of data into a single tissue map.

In further embodiments of the invention the instrument further creates an orthotic, prosthetic or cushioned surface.

In further embodiments of the invention the orthotic, prosthetic or cushioned surface created serves to protect diseased tissue or tissue at risk for disease.

Other embodiments of the invention can comprise a method for diagnosing a tissue comprising:

collecting first information on pressure or shear stress of said tissue;

collecting second information on tissue oxygenation, tissue metabolism or tissue perfusion information of said tissue; and combining both first and second information to identify portions of said tissue that are diseased or susceptible to disease In further embodiments of the invention the method provides information about the tissue of a patient which is then used in modifying the environment of a patient or treat disease of said tissue.

Other embodiments of the invention can comprise a method for treating a disease or disorder comprising:

combining information regarding pressure or shear stress on a tissue with tissue oxygenation, tissue metabolism or tissue perfusion information of said tissue;

identifying from the combined information portions of said tissue that are diseased or susceptible to disease; and modifying the environment of a patient to prevent or treat the disease or disorder.

Other embodiments of the invention can comprise a method of ameliorating a disorder by determining a physiological state of a tissue comprising:

determining tissue oxygenation, tissue metabolism or tissue perfusion information of said tissue;

determining pressure or shear stress on said tissue;

identifying areas of the tissue or corresponding aspects of the physical stress that are indicative of susceptibility to disease; and modifying an environment around said identified susceptible tissue.

DESCRIPTION OF THE INVENTION AND EXAMPLES

The present invention now will be described more fully hereinafter with reference to preferred embodiments of the invention. This invention may, however, be embodied in many different forms and should not be construed as limited to the embodiments set forth herein; rather, these embodiments are provided so that this disclosure will be thorough and complete, and will fully convey the scope of the invention to those skilled in the art.

Embodiments of the invention combine in-vivo spectroscopy and hyperspectral technologies with an understanding of physiology, wound care, foot care and conditions and the clinical management of people with diabetes, peripheral vascular disease, venous disease and metabolic disturbances or other medical conditions that impair wound healing or tissue integrity.

When referring to Hyperspectral technologies and/or hyperspectral imaging, such also includes multispectral imaging.

In one embodiment a tissue oxygenation map as measured by hyperspectral technology (HT) is used by itself or in combination with contour or pressure maps to define areas of tissue at risk of ulceration. An HT map is designed to show the spatial distribution of oxyhemoglobin and deoxyhemoglobin in tissue. The pseudo-colors and brightness level presented in the image depend on the levels of these two components as determined on a pixel by pixel basis. Sites having low values of oxyhemoglobin (high risk) are typically depicted as grayish yellow while areas of high oxygenation are reddish purple.

Tailored orthotics (insoles for shoes as one example) can then be designed that offload pressure at selected sites identified as high risk. Pressure maps as measured by force plates and contours as measured by scanning methods or from casts can be further used to distribute the remaining pressure to the rest of the foot. The tailored orthotics can take the shape of the foot while having areas designed to offload pressure at selected sites. The insole can be made with a high density plastic or rubber material with a lower density foam or polymer at the sites at risk. Pockets of silicone gels or fluids can be used to further reduce impact pressures.

HT maps taken while a patient is standing barefoot, walking barefoot or taken with no weight placed on the foot, as when seated or lying down, each provide different information as to the relationship between pressure and adequate tissue perfusion. In one embodiment, HT maps are taken with the patient seated or lying down, with no weight bearing. This information is then paired with digital or digitalized data obtained from pressure or contour measuring devices in order to generate an advanced orthotic. Image registration techniques are used to fuse the images and an algorithm applied to instruct the orthotic any one or any combination of these measurements is used to assess the adequacy of tissue perfusion to optimize an orthotic for use under real world conditions.

Figure 1:
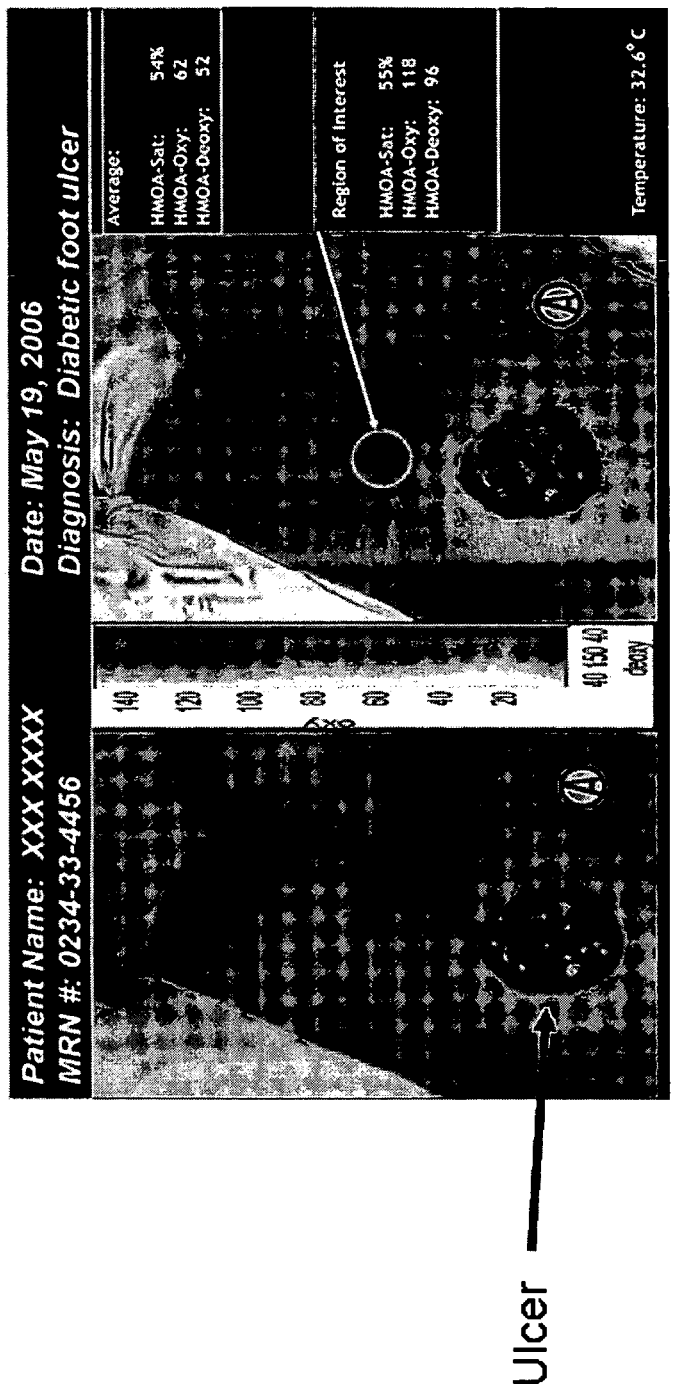
FIG. 1: The image illustrates a normal foot with characteristically lower HT values seen in the absence of a wound. Note the registration target that allows the proper registration of sequential scans to form the tissue maps presented. In this image a pressure point is denoted cause by recent pressure from a tightly fitting shoe.

In another embodiment, images of the foot taken after walking in a given shoe, footwear, or orthotic is used to determine points of increased irritation of the foot to assist in optimizing the footwear. FIG. 1 shows an HT map which demonstrates a pressure point created by suboptimal footwear. This map provides novel information for use to modify standard methods of orthotic or footwear construction to relieve pressure in areas identified by HT mapping. In FIG. 1, the tissue is not on the foot sole, and standard methods to create an orthotic pressure measurement or molding while standing would not address this area on the lateral/dorsal foot surface.

In another embodiment of the invention, HT maps is obtained of an amputation stump either with or without weight bearing and with or without exercise for evaluation of an existing prosthesis or design of a new one.

Figure 2:
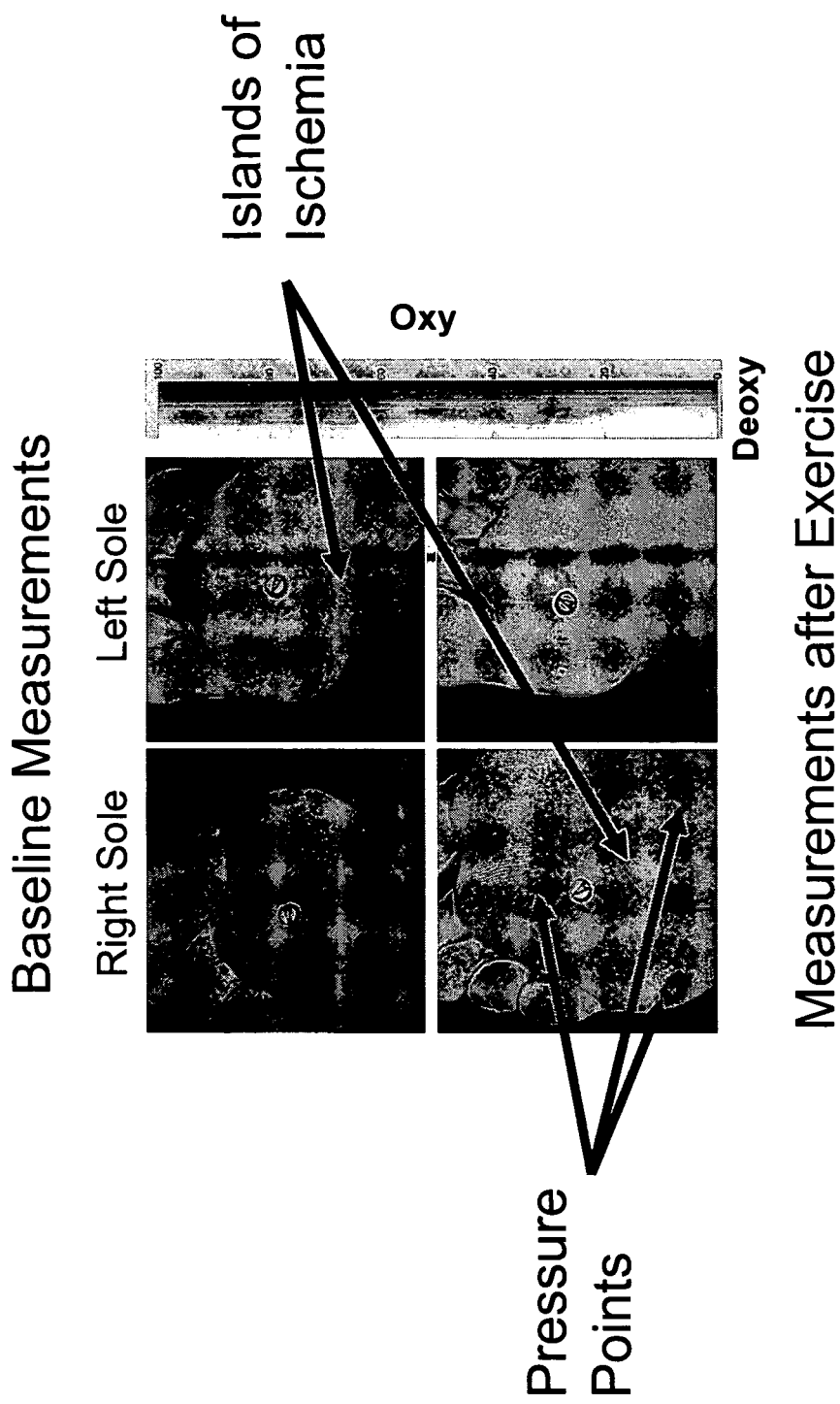
FIG. 2: Picture of claudicated foot at baseline and after exercise. HT mapping of a mild/moderate claudicator with pain while functioning as a facilities maintenance man during his work day. Angiography showed evidence of L common femoral artery occlusion. Long segment occlusion precluded successful angioplasty/stent. The study showed reconstitution before the SFA/profunda bifurcation with good distal runoff. The top row demonstrates changes due to vascular compromise seen at baseline, including an "island of ischemia" in the center of the left forefoot. Before we started the study the subject pointed to this region as the place that had dysesthesias and discomfort long before claudication started. The bottom row shows dramatic changes after brief exercise (until pain occurred while he was carrying a box and walking briskly for 1 minute, which is typical of his work requirements). An island of ischemia is observed in the right foot following exercise.

In another embodiment of the invention, the HT map is obtained after exercise on a treadmill. FIG. 2 demonstrates a patient with left leg claudication with an obvious "island of ischemia" demonstrated by a localized region of low oxyhemoglobin readings on the HT map of his left foot sole at rest. After exercise perfusion is globally decreased, but the central region where the tissue is most at risk is enlarged. The right foot, which has no major abnormalities at rest, demonstrates an area of decreased tissue oxygenation after exercise. This HT map after exercise can be used in conjunction with contour or pressure measurements to create optimized footwear.

Measurement of tissue perfusion, oxygenation, oxygen delivery or oxygen extraction by HT provides additional information to assist the physician in early diagnosis, prevention, treatment selection and treatment monitoring in such a way as to provide benefit to patients with tissue breakdown or those at risk for tissue breakdown.

In one embodiment, HT maps are taken when pressure is off of the area of interest and compared with those taken after the area of interest is positioned on a given surface. This is used for modifying the surface or providing cushioning in appropriate locations. In one embodiment this takes the form of a specifically contoured "doughnut". In another embodiment the HT map provides information relative to the adequacy or inadequacy of the bed or wheelchair padding or pressure and provides information or recommends local modifications of the surface supporting the body to minimize pressure in areas most at risk. For example, an HT map of a paralyzed patient's buttocks is taken while lying prone and then again after sitting in his wheelchair. Pressure points noted by HT are identified and the chair contour or consistency of material modified in these regions. Because of the spatial map generated by HT has a spatial resolution of 100 microns, the contour of the seating material can be very precisely constructed.

In another embodiment, in the evaluation and treatment of a sacral decubitus ulcer, in addition to removing pressure from the region of the ulcer, HT measurements provide information about all of the surrounding tissue and the adequacy of perfusion elsewhere. In one embodiment HT measurements are taken with the patient prone and the ulcer and surrounding skin in the baseline, non weight bearing state. In another embodiment HT measurements are taken from underneath the surface, through a transparent surface on which the patient is lying. In a third embodiment, two sets of HT measurements are taken, one while the tissue is not exposed to weight bearing and one after the patient was lying on whatever surface was used to position him/her. In another embodiment, a feedback loop is created to develop a "smart bed" or "smart cushion" which was transparent and allowed for measurement of HT in real time. In this embodiment, as tissue oxygenation decreases in a certain region due to pressure, the bed or cushion would shift its properties to decrease pressure on areas of decreased perfusion. This is done by hydraulic, air pressure, thermal or other means. In another embodiment HT mapping information is utilized to direct the administration of other therapies to alter the relationship between oxygen delivery and oxygen demand in any given region such as providing heat, cooling, vasodilators, or other pharmacologic agents.

This can also occur following a variety of surgical procedures including those in which a portion of the patient is casted or positioned in a particularly chosen position.

Patients with early stage peripheral vascular disease with only the early manifestations of mild claudication may have islands of ischemia visible by HT either at rest or after exercise as on a treadmill. These patients may benefit from either earlier angiography and endovascular or vascular surgical repair or by construction of orthotics or footwear that protects the areas demonstrated either before or after exercise to have a decrease in HT measurements of tissue oxygenation.

HT oxygenation mapping combines information about oxyhemoglobin and deoxyhemoglobin into a two dimensional colorized representation. One embodiment of the invention speaks to the use of HT oxygenation mapping for the adjustment of pressure on tissue regions to prevent tissue breakdown. Tissue demonstrated to be at risk by HT oxygenation mapping is treated by delivering reduced pressure to the site, by delivering reduced pressure to the site, by delivery of additional pressure to the site (as in the case of venous ulcers or to instill medications), by delivery of essentially zero pressure to the site or by delivery of negative pressure to the site.

HT measurement is combined with pressure measurements obtained from the sole of the foot while standing or walking or from any other body part that is in prolonged contact with a surface such as a wheelchair or bed.

For measuring pressure or contour of the foot, in general the patient stands or walks on the device, however similar pressure measurements can be taken by placing a pressure measuring pad or device in a shoe or orthotic for continuous measurement. In one embodiment, HT measurements are combined with pressure measuring techniques in an index map that reflects both measurements. To do so, HT measurements and an image of the foot created by one of the pressure measuring techniques are co-registered into a single index map. In another embodiment, modifications of the HT measurement system optics and instrumentation are undertaken to acquire data from underneath the patient's foot while standing simultaneously with measurements of tissue contour achieved with a NIR scanning technique. The images will be co-registered and an algorithm for synthesizing the pressure and tissue oxygenation or perfusion data will be utilized to generate an index map which delivers an optimized pressure profile for orthotic, footwear, prosthetic or cushion construction.

In another embodiment, the pressure measurements could be done with pedobarograph or other pressure measurements and HT maps being performed sequentially and then integrated later. If the pressure measurement technique provides a hard copy of the information not in digitized format, one embodiment of the invention will scan in the pressure data, place in digital format, coregister with HT mapping data, run an algorithm for synthesizing the pressure and tissue oxygenation or perfusion data to generate an index map which delivers an optimized pressure profile for orthotic, footwear, prosthetic or cushion construction.

Similar measurements can be taken by placing a pressure pad on the bed or wheelchair surface of a debilitated patient to demonstrate areas of increased pressure on the skin due to bony structures or body conformation. In another embodiment, a clear surface is used and NIR scanning provides contour information for use in conjunction with HT maps as described above.

In one embodiment, modification of the surface or device to alter the pressure on the tissue can be undertaken on the basis of HT mapping data alone, which inherently contains some data related to pressure or shear stress on the tissue. In another embodiment, the combination of HT maps or other oxygenation or perfusion information with tissue pressure or contour information are used to modify the surface or device to alter the pressure on the tissue.

In one embodiment, a "smart system" can be created to obtain HT data in a continuous or intermittent fashion and the pressure can be automatically adjusted either continuously or intermittently based on the HT map or other oxygenation or perfusion measurement. In another embodiment, a care giver can obtain the information and make the adjustments to the pressure modifying device.

One embodiment of the invention here pertains to utilizing HT mapping to identify areas of tissue most at risk and combining this with contour or pressure mapping data that has been used to apply uniform pressure, to design orthotics or cushions to deliver pressure tailored to the needs of the tissue.

In other embodiments, HT mapping will be paired with any of the following pressure measuring techniques. To do so appropriate modifications of both the HT instrumentation and the pressure measuring devices will be undertaken to achieve data most useful for combination. Unique algorithms will be required for pairing with any one of the specific devices or technologies listed:

Tekskan system
Video pedobarograph system
Podotrack
Optical pedobarograph
PressureStat
Kistler force platform
Spiral computed tomography and planar pressure measurements
KScan System
Prosthetic System
Grip System
Hoof and Saddle System HT mapping demonstrates pressure points in most patients by delivering measurements with increases in tissue oxygenation and total hemoglobin to the area. In some patients with ischemia, pressure points are manifest by a decrease in tissue oxygenation and total hemoglobin from baseline after exercise.

In one embodiment HT mapping is combined with data derived from a method of measuring pressures and forces applied to the foot is via an ultrasonic method. Here, simultaneous measurement of force applied to the tissue during a quasi-static computer controlled compression and ultrasonic images of the underlying bone are obtained. In this technique, a cylindrical pexiglassrod is attached to the end of an trasound probe. A force transducer is mounted with the probe, and the plexiglass rod is slowly advanced into the tissue until the applied pressure reaches a specified amount (such as approximately 400 kPa).[50] HT maps are recorded as are ultrasonic images of the foot and the magnitude of the applied force are continuously recorded throughout the experiment. These data are then used to construct force-displacement curves and combined pressure/oxygenation index maps of the tissue.

In another embodiment, HT mapping could be integrated into the biomechanical assessment of human-based load carriage system assessment for the objective evaluation of biomechanical aspects of load-bearing webbing, vests, packs and their components.[51]

Another embodiment combines HT mapping or tissue perfusion measurements with an instrument] devised for the in vivo examination of the dynamic biomechanical stiffness and viscoelasticity properties of skin such as the dynamic biomechanical skin measurement (DBSM) probe described by Elizabeth K Dawes-Higgs et al.[52]

Another embodiment combines HT or other tissue oxygenation or perfusion information with mapping data generated by a compound ultrasound sensor and pressure transducer system such array system described by Wang et al.[53] for use in the measurement of buttock soft tissue in vivo to assess susceptibility to pressure ulcer formation.

Another embodiment combines HT or other tissue oxygenation or perfusion information with pressure and/or shear stress and/or ambulatory motion information provided by videofluoroscopy,[54] spiral CT scan[55] of the amputated extremity or pressure measuring pads, transducers other or devices placed in prosthetic devices in order to optimize prosthetic fit and prevent complications.

Another embodiment of the invention is directed to a method of measuring tissue oxygenation changes associated with tissue ischemia or damage. HT measurements are used to demonstrate not only tissue oxygenation but also adequacy of oxygenation for the tissue to either remain viable (in the as yet uninjured situation) or to heal if an ulcer or area of breakdown is already present. HT provides information regarding both tissue perfusion and metabolism, displaying images that identify specific areas of the foot or other tissue that may be at risk for ulceration, and deliver information to the physician to assist him in identifying specific protective measures to lower the risk of ulcer formation, such as orthotics or offloading. By measuring not only tissue perfusion, but the adequacy of that perfusion, HT is also used to quantitatively determine the spatial distribution of well and poorly perfused regions of the skin on the foot and thereby determine which regions of the foot are susceptible to ulceration. Changes in these regions may be tracked over time.

Hyperspectral imaging has several features that may lead to it becoming a valuable technique for screening and evaluation of the foot in diabetes and other peripheral vascular disorders. Among other capabilities, hyperspectral imaging technology can identify and assess areas of tissue at risk and islands of ischemia. Point measurements such as TcPO2 or global measurements such as duplex scanning, PVR or ABI will not identify such problem areas. In one embodiment, however, the orthotic design is modified by applying a scalar value associated with one of the point measurement or regional measurement techniques described above.

HT oxygenation mapping combines information about oxyhemoglobin and deoxyhemoglobin into a two dimensional colorized representation. One embodimenet of the invention speaks to the use of HT oxygenation mapping for the adjustment of pressure on tissue regions to prevent tissue breakdown. Tissue demonstrated to be at risk by HT oxygenation mapping could be treated by delivering reduced pressure to the site, by delivering reduced pressure to the site, by delivery of additional pressure to the site (as in the case of venous ulcers or to instill medications), by delivery of essentially zero pressure to the site or by delivery of negative pressure to the site.

HT measurement could be combined with pressure measurements obtained from the sole of the foot while standing or walking or from any other body part that is in prolonged contact with a surface such as a wheelchair or bed.

Measurements that measure pressure or contour of the foot have been described .... In general the patient stands or walks on the device, but similar pressure measurements can be taken by placing a pressure measuring pad or device in a shoe or orthotic for continuous measurement.

Similar measurements can be taken by placing a pressure pad on the bed or wheelchair surface of a debilitated patient to demonstrate areas of increased pressure on the skin due to bony structures or body conformation Modification of pressure to tissue can be undertaken on the basis of HT mapping data or on the combination of HT maps or other oxygenation or perfusion information with tissue pressure or contour information.

In one embodiment, this can occur in a continuous fashion and the pressure can be automatically adjusted based on the HT map or other oxygenation or perfusion measurement.

Other embodiments can include the prevention of further disease, diagnosis of disease, the monitoring of therapy, and a general assessment of microvascular status and progressive of disease.

Prevention:

HT processes both perfusion and metabolic data, thereby displaying images that identify specific areas of the foot that may be at risk for ulceration, and thereby lead to institution of specific protective measures to lower the risk of ulcer formation, such as orthotics. HT is used to quantitatively determine the spatial distribution of well and poorly perfused regions of the skin on the foot and thereby determine which part of the foot is susceptible to ulceration. By tracking non-visible changes over time HT provides early warning of the need for additional non-surgical intervention.

Diagnosis:

In the patient with a visible foot ulcer, HT mapping defines a level of tissue ischemia which would make debridement unsafe. A reduction in tissue oxygenation will allows the doctor to determine whether the ulcer will heal or will require some level of amputation to close the wound.

Monitoring of Therapeutics:

HT can determine and objectively quantify the size, shape and severity of existing ulcers to monitor the efficacy of treatment. Additional potential strengths of hyperspectral technology include the ability to repeat studies periodically to obtain objective longitudinal follow-up.

Assessment of General Microvascular Status/Progression of Disease:

Hyperspectral technology provides information about microcirculatory disease that cannot be assessed by conventional visualization techniques. It is useful at both the research and direct patient care level. Given that an abnormal ABI has been shown to be associated with increased risk of cardiovascular disease and death, HT may be even more useful as an early screening test for coronary artery disease and stroke in patients with diabetes. It also provides information relative to neuropathy and its progression.

Although not every diabetic foot disorder can be prevented, it may be possible to effect dramatic reductions in their incidence and morbidity through appropriate prevention and management tools. Routine application of a simple non-invasive monitoring device over the extended period of disease of patients with diabetes will prove especially useful.

Medical Hyperspectral Technology (HT) delivers information at the level of the tissue which combines influences from the local surrounding, from physiology or pathology related to the macrovessels responsible for regional blood flow and from systemic microvascular status, both baseline and as affected by medications, state of hydration, anemia, etc. HT specifically examines the microvasculature that is thought to be one of the prime targets of hyperglycemic damage. HT provides information and diagnostics to assist in research on improving local or systemic therapies useful in prevention of foot ulcers and other microvascular complications. HT has the potential of becoming a standard clinical tool for the definition of tissue at risk and the prediction or early detection of vascular foot and tissue lesions, wounds and ulcers of ischemic, neuopathic, venous or other origins more than just foot. By tracking non-obvious changes over time, early warning by HT provides the foundation for preventing the occurrence of ulcer formation by the institution of specific therapies or protective measures such as orthotics or define the need for revascularization procedures.

HT can detect clinically significant changes in the cutaneous microvascular circulation and in tissue properties of the feet of people with diabetes at an early stage, and these changes can be used to predict the subsequent risk of foot ulceration. Studies were performed in three phases to further understanding of the disease.

Individuals having diabetes type 1 or type 2, or other diseases or infirmities which may lead to foot or skin ulcers as a result of improper oxygen saturation levels may use HT for prevention or reduce the potential for the development of such ulcers. In the past, much of the diagnosis and emphasis for reducing the occurrence of ulcers, especially plantar ulcers, focused on the distribution of plantar pressure as the primary cause or indicator of resulting ulcers. However, HT widens the focus to the view tissue oxygen delivery, oxygen extraction and oxygen saturation as a contributing cause of ulcers.

The technique is noninvasive, rapid, and can be performed during regularly scheduled office visits without the necessity for prior patient preparation. The clinical procedure takes under a minute and requires little more than positioning the patient carefully and taking a pre-programmed series of images at various wavelengths of light with the hyperspectral camera. HT information is useful in three main areas of patient care: prevention of disease, anatomic diagnosis, and monitoring of therapy. In each case utility is for both research and clinical applications.

Therefore, HT can be used to identify areas of high risk for the potential outbreak of ulcers, especially plantar ulcers. HT can be used to generate a gradient map or index map of the plantar region of the foot, or other areas of interest. The HT map can show the tissue oxyhemoglobin, deoxyhemoglobin and oxygen saturation levels of the area of the tissue analyzed. Low levels of oxygen saturation can indicate a high risk for onset of ulcer formation. The determination of low levels of oxygen saturation can be determined by comparing different points the HT image where lower level regions can be indicative of high risk. Furthermore, testing can be conducted over time and comparing the relative change of oxygen saturation in an individual's foot. Furthermore, oxygen saturation levels can be compared between one person's feet, or there can be a large sampling of individuals to establish a baseline level of appropriate oxygenation. However, as described elsewhere, oxygenation and ulcer formation can be highly dependent on an individual's own characteristics.

Evaluation of high risk areas can be conducted on the basis of HT data alone, that is oxygen saturation, or in combination with pressure data as well. Pressure distribution of the foot combined with information regarding tissue perfusion, oxygenation or oxygen saturation can result in greater confidence in preventing ulcer formation.

Once high risk areas have been determined, orthotics can then be applied as part of the methodology of preventing ulcer formation. In the past, orthotics has been directed merely to alleviating high pressure areas, or equalizing pressure of the plantar region of the foot. However, by identifying high risk areas based on HT data, orthotics can be directed to redistributing pressure to alleviate low tissue oxygenation or oxygen saturation areas. In preferred embodiments, it is desirable to have no pressure, or as little pressure as possible on such poorly oxygenated or perfused areas. However, additionally, pressure data can be also taken into account in pressure redistribution. Not only HT data is taken into account, high pressure areas can be taken into consideration to redistribute pressure in such a way that high pressure areas are alleviated as well as low oxygenation areas.

Pedobarograph System

1.) Optical force plates (U.S. Pat. No. 5,722,287)—a video gait analysis system used to measure the pressure at the bottom of the foot through all the stages of the gait cycle. While walking across a force plate fitted with an illuminated glass plate, the pressure from each step deflects the glass plate which in turns reflects the illumination light downwards. The reflect light is capture with a video camera and is proportional to the force of the foot hitting the plate. System can measure static and dynamic (while walking) pressures.

2.) Electrical Force plates—Capacitive pressure 1344 sensors from Novel Inc, Germany having 2 sensors per square centimeter, F-Mat/F-Scan having 1.4 sensors per square centimeter (TekScan, Boston), or similar technology can be used as the force plate. Interpolation of the data produces high resolution isobarographs. System can measure static and dynamic (while walking) pressures.

3.) Pressure sensitive ink sheets—Semi-quantitative as low cost alternatives to force plate pedobarograph. Identifies high pressure ($>12.3$ $kg/cm^2$) areas on the plantar surface. Based on ink impression sheets, a pressure chart is used to quantify pressure. Sheets can be used to measure static and dynamic pressures. Examples include Podotrack (Foot Care Technology) and PressureStat (Footlogic, Inc.).

The current invention proposes a new means for measuring the plantar pressure by creating by hyperspectral technology a tissue oxygenation map of the foot tissue at baseline. In a separate embodiment, the invention measures the change in tissue oxygenation while standing on or walking across a transparent platform, or on a surface that measures pressure while walking or standing.

Hyperspectral imaging can also be used in combination with the above technologies to assess tissue for the risk of ulceration, especially when evaluating the feet of patients with diabetes and/or peripheral arterial disease. The HT map can be used to identify pressure points on the tissue surface and an orthotic insole can then be designed where the pressure at this site is reduced or offloaded.

Combining hyperspectral technology with contour or pedobarographic methods can be done sequentially or in some cases simultaneously. For sequential measurements, the HT map can be overlaid on the contour or pressure maps using image registration techniques. Sequential methods are more relevant when recording dynamic pressure or other forms of measurements. Offloading would be advised in cases where areas of high pressure coincides with low tissue oxygenation.

In another embodiment, simultaneous HT mapping is coupled with optical contour or optical pedobarographic measurements. Contour mapping by optical scanning of the foot and hyperspectral mapping can be done having nearly coincidental optical axes. Both imaging systems would be housed underneath the transparent platform.

Figure 3:
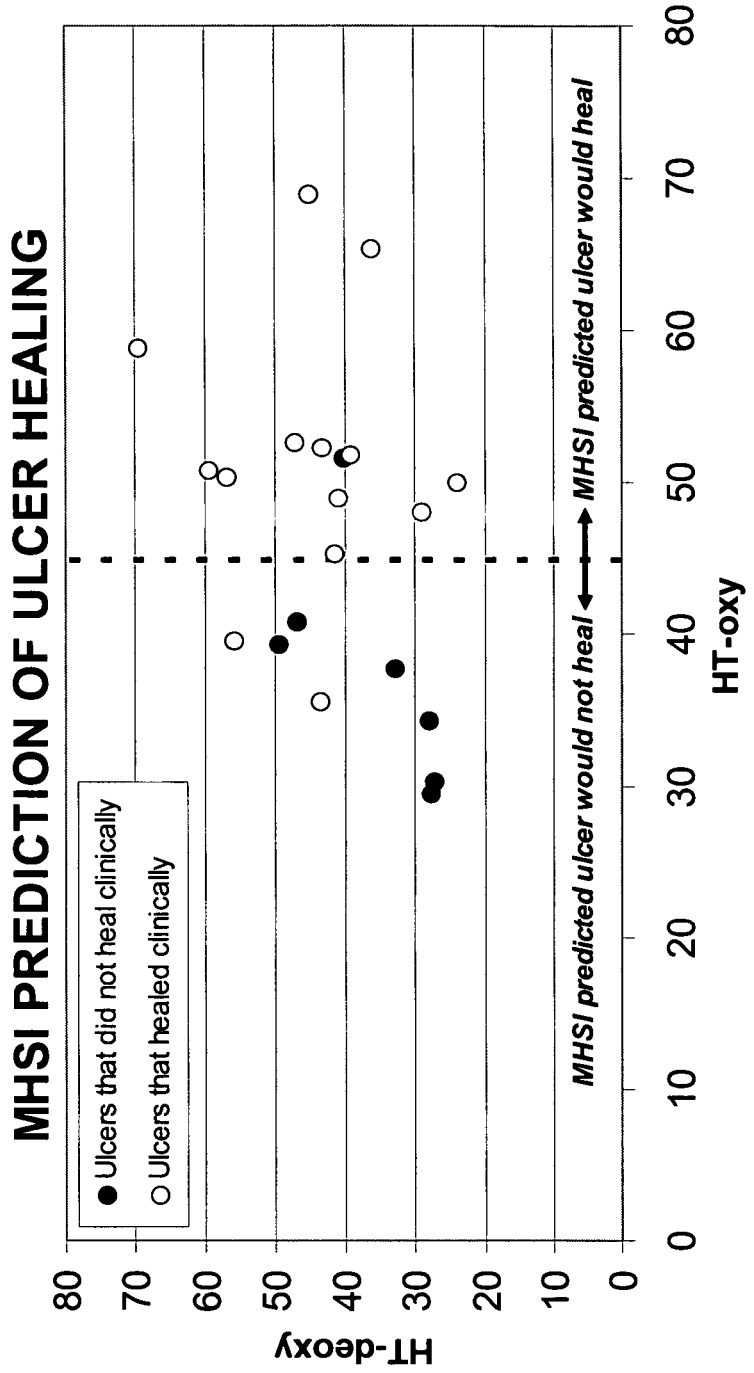
FIG. 3: Ulcer healing prediction algorithm using HT-oxy≥45 to predict healing in ulcer subjects from Phase I. If HT COM-OXY is greater than 45, then it is likely the ulcer will heal.
Figure 4:
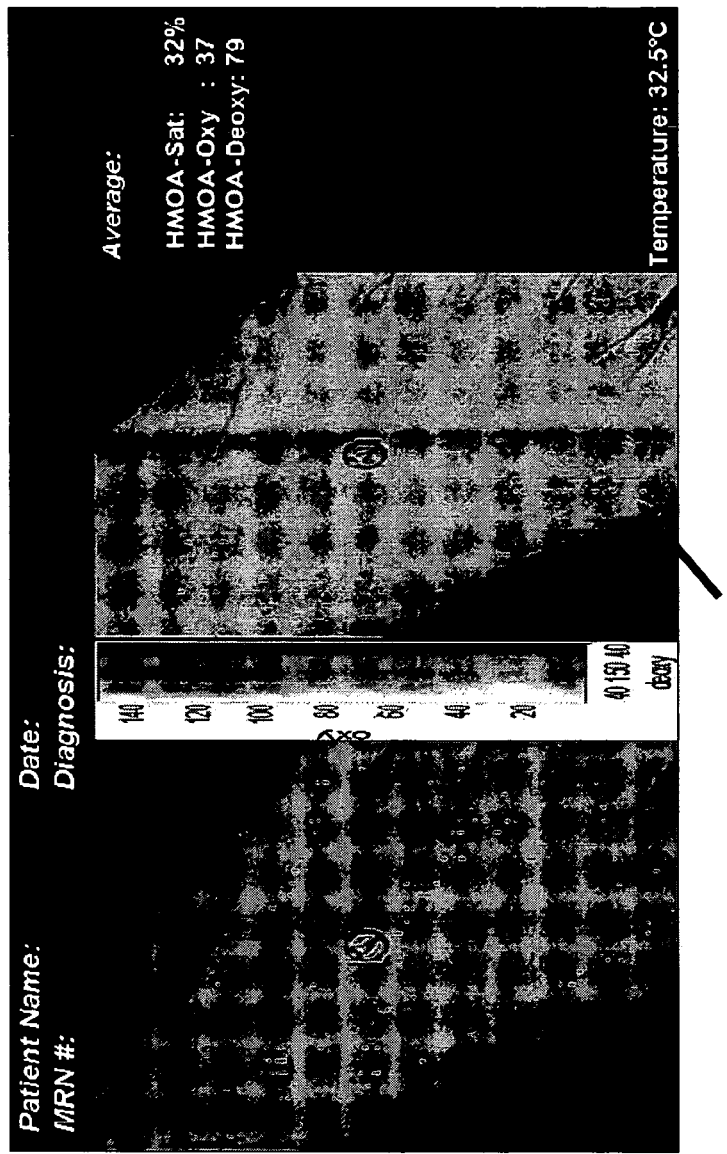
FIG. 4: Type 1 diabetic subject with a deep ulcer located under the $1^{st}$ metatarsophalangeal joint. The Left Panel presents the color image of the ulcer. This image demonstrates use of a mosaic formed from two separate images and a method of analysis using a radial map and segments around the ulcer. The right image shows the hyperspectral composite image with a radial map centered on the ulcer. The radial map has 20 circles spaced 1 mm apart that are divided into 8 segments forming a maximum of 200 segments in which the mean values of oxyhemoglobin and deoxyhemoglobin are calculated and presented.

Clinical Data:

In summary, over 3500 clinical HT values have been collected and data have been published in the *Lancet, Vascular Medicine and Diabetes*.[44, 56, 57] HT provides more clinically useful information about tissue microcirculation and pathophysiology than other methods. HT values correlate with ulcer healing (FIG. 3) with both a sensitivity and specificity of 86%, and vascular symptoms correlate significantly with HT values ($p<0.01$).[56] HT reveals significant pathologic impairment in the microvasculature of the feet of diabetic patients which is accentuated in the presence of neuropathy. Differences in the underlying microvasculature of diabetics also are found in the forearm, and it has been concluded that these microvascular changes contribute to the development of foot ulceration and could preclude the healing of existing ulcers.

Micro- and macrovascular abnormalities of the diabetic foot were studied in collaboration with Dr. Aristidis Veves and colleagues at the Microvascular Laboratory at Harvard's Beth-Israel Deaconess Medical Center. Data were presented on 108 subjects divided into healthy non-diabetic subjects, non-neuropathic diabetic subjects and neuropathic diabetic subjects collected under funding from the American Diabetes Association.[44] Changes in large vessels and microcirculation of the diabetic foot play an important role in the development of foot ulceration and subsequent failure to heal existing ulcers and we evaluated the correlation of HT data with the circulatory status of tissue with diabetes and sub-populations at greater risk for foot disease. The paper describes significant changes in oxygen delivery & extraction reported by HT measurements of the skin of the forearm and foot of diabetic patients, with or without neuropathy.

During HT measurements, the baseline oxyhemoglobin (HT-Oxy) was reduced in both non-neuropathic and neuropathic groups compared to controls ($p<0.0001$). Resting deoxyhemoglobin (deoxyHb) showed a non-significant inverse trend in control, non-neuropathic and neuropathic group (p=NS). Tissue hemoglobin oxygen saturation ($S_{HT}O_2$ or HT-Sat was different among all three groups, being highest in controls followed by non-neuropathic and neuropathic groups ($p<0.001$).

Similar results were observed in the measurements at the dorsum of the foot. However, the main differences with the forearm results were that the baseline HT-Oxy was reduced in the neuropathic group when compared to non-neuropathic and control groups ($p<0.0011$) As a results of this, the baseline HT-Sat was higher in the controls and non-neuropathic compared to the neuropathic group ($p<0.05$).

The conclusions drawn from these data were that:
1) HT measurements performed at the forearm level provide a measure of the systemic microvasculature, as the forearm represents an area that is traditionally not differentially afflicted by microvascular or macrovascular disease to the extent of the lower extremities;
2) HT measurements performed at the dorsal foot surfaces, in turn, provide regional information, potentially indicative of both microvascular and macrovascular changes associated with atherosclerotic disease in large vessels exacerbated by diabetes and that HT is able to differentiate the level of this damage on either the right or left lower extremity; and
3) skin oxygenation is impaired in the diabetic foot and this may be major contributing factor for the observed impaired wound healing of the diabetic foot ulcers. These data suggest that HT measurements can provide physiological information about the baseline condition of tissue that is relevant to determining the wound healing capacity of a given individual or given extremity.

Iontophoresis Studies

Microvascular reactivity measurements have been performed using iontophoresis at both the forearm and dorsum of the foot level of the non-dominant side. This ensures the testing of an area that was not usually affected by neuropathy (forearm) and affected area (dorsum of the foot). The term iontophoresis denotes the introduction of soluble ions into the human skin by applying electric current. It is a non-invasive technique, which avoids any systemic effects of the used drugs. By applying acetylcholine chloride, the endothelium-dependent vasodilatation may be measured, while the use of sodium nitroprusside measures the endothelium-independent vasodilatation. The MIC1 iontophoresis system (Moor Instruments Ltd, Millwey, Devon, England) is used in this invention. Specifically, a small quantity (<1 ml) of 1% acetylcholine chloride solution is used on the forearm of the participating subjects; subsequently a constant current of 200 microampere will be applied for 60 seconds achieving a dose of 6 mC-cm-2.

The erythema typically takes the form of a uniform redness under the wrist strap electrode, while under the drug containment electrode, the tissue may exhibit either uniform or mottled redness. In order to avoid the measurement of a non-specific response to the vehicle (de-ionized water), both the response to the vehicle and to the active substances will be measured. The dose-response curves have been previously established for acetylcholine and nitroprusside in healthy subjects. Research experiments were designed to create two distinct alterations in cutaneous physiology by iontophoresis of two vasodilators: 1) sodium nitroprusside (endothelium independent); and 2) acetylcholine chloride (endothelium-dependent).

HT provided quantitative information over the physiologic range of local changes in the microcirculation of the foot induced by focal iontophoretic application of the endothelial dependent and endothelial independent vasodilators nitroprusside or acetylcholine.

The iontophoresis study demonstrated that HT tissue oxygenation maps change significantly and quantitatively during vasodilatation and confirm existing laser Doppler imaging (LDI) data that the microcirculatory responses of type 1 and type 2 diabetic feet. HT methods of determining the tissue oxygenation and relative oxygen saturation and total hemoglobin content in skin give results that are correlated with laser Doppler imaging (LDI)methods. However, LDI and HT measure different physical properties (LDI measures blood flow while HT measures oxy and deoxyhemoglobin that contribute to oxygenation status and total amounts of hemoglobin).

The use of HT mapping following iontophoretic application of vasodilators constitutes another embodiment. An iontophoretic vasodilator model was used successfully to study the microvasculature of diabetics by Drs. Veves, Arora and others.[58, 59] We obtained HT maps of oxyhemoglobin, deoxyhemoglobin, relative hemoglobin (Hb) concentration and O2-sat (hemoglobin oxygen saturation) from in vivo spectra of the skin before and after iontophoresis of endothelial independent and endothelial dependent vasodilators nitroprusside (NP) and acetylcholine (ACh). Skin spectra show the characteristic doublet of oxyHb as their major spectral feature. Control spectra were taken from a region not infused with the drug, while the green were taken from a NP infused region. Comparison shows the increase in oxyHb in the spectra following NP iontophoresis. These data demonstrate the utility of HT in monitoring drugs that cause vasodilatation such as antihypertensives and cardiac unloading agents. Similarly, HT can be used to monitor the effects of systemic or locally applied vasoconstrictors.

Following iontophoresis of ACh or NP, there is an increase in the O2-sat levels and an increase in total Hb determined by HSI in the areas affected by the drug infusion.[44] By fitting the reference oxyHb and deoxyHb spectra into the subject's spectra, an O2-sat percentage and a measure of total hemoglobin (tHb) are obtained for each pixel in the image. Subtracting the pre-iontophoresis O2-sat and Hb images from the correlative post-iontophoresis images enables the determination of the percent change.

Following iontophoresis of ACh or NP, there is an increase in the oxyhemoglobin, a decrease in the deoxyhemoglobin, an increase in O2-sat levels and an increase in total Hb determined by HT in the areas affected by the drug infusion.[44] This quantifies the visible reddening of the skin seen in the same regions. The increase of total Hb as measured by HT is comparable to the blood flow changes seen in laser Doppler imaging but with far improved spatial resolution.[44, 60] The O2-sat information offers the more important information as to the oxygen extraction by the tissue. In the face of vasodilatation, these images confirm the theory that with tissue metabolism relatively constant and an increase in local blood flow we will see less oxygen removed per unit of blood passing through the tissue and a relative increase in the oxyHb to deoxyHb ratio.

These results show that HT has the sensitivity and specificity to operate in the range of change that occurs physiologically in this model and can be used to monitor changes in blood flow and O2-sat in-vivo following iontophoresis. The spatial distribution of O2-sat and Hb following drug application is of particular interest. The increase in both relative O2-sat and total Hb appears to be more diffuse for ACh than for NP. The total Hb here reflects the total blood present in the region of interest, whereas the O2-sat image reflects more closely the increased oxygen delivery as well as oxygen extraction and metabolic state of the tissue.

In another study, HT measurements were acquired from the feet of 12 men at the VAMC in Washington, D/C. A typical subject required 20 minutes to be scanned at 4 sites on their feet (dorsal and plantar surfaces of each foot). HT data were acquired and processed as described below. To simplify initial analyses in this pilot, we collapsed these data as follows to obtain a single intensity for both relative O2-sat and tHb at each site on the foot.

Two sites on each plantar foot were chosen, the skin directly above the 1st and the 3rd metatarsophalangeal joint (MTPJ). For each site on each foot, both the relative O2-sat and total Hb values as determined from the HT data were averaged within an approximately 1 cm² area. These data are summarized below in the following Table.

| Variable by Site | Mean | Std Dev | Minimum | Maximum | Sample Size |
|---|---|---|---|---|---|
| Relative Oxygen Saturation | | | | | |
| Left 1st MTPJ | 37.19 | 7.28 | 26.36 | 48.07 | 12 |
| Right 1st MTPJ | 37.04 | 9.00 | 23.83 | 54.92 | 11 |
| Left 3rd MTPJ | 35.24 | 8.92 | 17.43 | 48.93 | 12 |
| Right 3rd MTPJ | 34.03 | 11.62 | 9.69 | 50.27 | 11 |
| Total Hemoglobin | | | | | |
| Left 1st MTPJ | 0.71 | 0.18 | 0.46 | 1.04 | 12 |
| Right 1st MTPJ | 0.66 | 0.17 | 0.37 | 0.85 | 11 |
| Left 3rd MTPJ | 0.67 | 0.20 | 0.36 | 0.99 | 12 |
| Right 3rd MTPJ | 0.71 | 0.22 | 0.26 | 1.19 | 11 |

One subject had had his right foot amputated. Thus, for relative O2-sat and for tHb, we obtained 12 measurements of left feet and 11 measurements of right feet at two foot-sites (hereafter site).

The age of the 12 males subjects ranged from 47 to 79 (with a mean of 62.4 and SD of 11.4 years). Among the 12 subjects, 6 had diabetes, 4 had coronary artery disease, 7 had hyperlipidemia, 6 were smokers, 6 were hypertensive, and 8 had claudication. This defined six binary factors; namely, diabetes, coronary artery disease, hyperlipidemia, smoker, hypertension, and claudication.

For each of these six we used the t-test to compare the two mean values for the categories 'condition present' or 'condition absent'. This was done for each relative oxygen saturation and total hemoglobin measure. Because age correlated with some of relative oxygen saturation measures, we re-ran these t-tests controlling for age.

Age significantly ($p<0.05$) correlated with relative O2-sat at the left 1st MTP J, right 1st MTPJ and left 3rd MTPJ sites with respectively $r=-0.70$-$0.69$-$0.81$, but not with tHb at any of the sites. Subjects with claudication had significantly lower mean values of relative O2-sat at the three sites and nearly significant at the right 3rd MTPJ site ($p<0.10$). For tHb, subjects with claudication had a lower mean value at the right 3rd MTPJ site, but it was not quite significant ($p<0.10$).

The mean O2-sat and total Hb measures did not differ with respect to any other binary factor (diabetes to hypertension). This negative result held when the comparisons were adjusted for age.

Next we defined a 'better' foot and a 'worse' foot for patients with two feet. The better foot had the higher average scan measurements over all sites for a combined measure of relative O2-sat and tHb, where relative O2-sat and tHb values were rescaled to make the values comparable. We also averaged left and right feet for these eleven subjects. For all six binary factors t-tests were run on each of these newly defined variables. There were significant results for only the factor, claudication. These claudication results held only for the oxygen measures, but did so at both the sites, 1st MTPJ and 3rd MTPJ. The t-tests were significant when comparing either the better foot or the worse foot. Only the average of the two feet at the 1st MTPJ site was significant.

The conclusions from these data were:
Relative O2-sat images appear more likely to distinguish between healthy and less healthy tissue in the feet than total hemoglobin
Relative O2-sat measures appear to distinguish subjects with and without claudication.
Although these results come from a sample where n=12, there is a strong indication that peripheral circulatory compromise, as evidenced by the early symptom of claudication, causes a decrease in the relative O2-sat level in the foot. This provides strong evidence that HT methods are useful in determining the vascular status of diabetic feet. Larger sample sizes will allow an exploration of the spatial heterogeneity of these results. We can track changes in tissue oxygenation correlating to claudication, which is very early in the progression of vascular compromise.

Clinical Diabetic Ulcer Study Results

The mean values for oxyhemoglobin, deoxyhemoglobin, and hemoglobin oxygen saturation are given in the following table for high risk diabetic subjects, low risk diabetic subjects and control nondiabetic subjects at baseline and post-iontophoresis. Bold-face values denote significant changes.

| Site | Group (N0 | HT —Oxy | HT —Deoxy | HT —Sat |
|---|---|---|---|---|
| Forearm - Baseline | Control (21) | 29 ± 7 | 41 ± 16 | 42 ± 17 |
|  | Low-risk diabetics (36) | 20 ± 5 | 44 ± 10 | 32 ± 8 |
|  | High-risk diabetics (51) | 19 ± 7 | 49 ± 10 | 28 ± 8 |
| Dorsum of Foot - Baseline | Control (21) | 25 ± 13 | 44 ± 18 | 38 ± 22 |
|  | Low-risk diabetics (36) | 24 ± 9 | 41 ± 11 | 37 ± 12 |
|  | High-risk diabetics (51) | 19 ± 9 | 45 ± 13 | 30 ± 12 |
| Forearm - Post-iontophoresis | Control (21) | 50 ± 12 | 52 ± 15 | 49 ± 10 |
|  | Low-risk diabetics (36) | 41 ± 8 | 50 ± 10 | — |
|  | High-risk diabetics (51) | 38 ± 9 | 50 ± 9 | 43 ± 7 |
| Dorsum of Foot - Post-iontophoresis | Control (21) | 47 ± 15 | 50 ± 17 | 49 ± 15 |
|  | Low-risk diabetics (36) | 39 ± 11 | 44 ± 11 | 47 ± 11 |
|  | High-risk diabetics (51) | 32 ± 9 | 47 ± 15 | 41 ± 10 |

Figure 5:
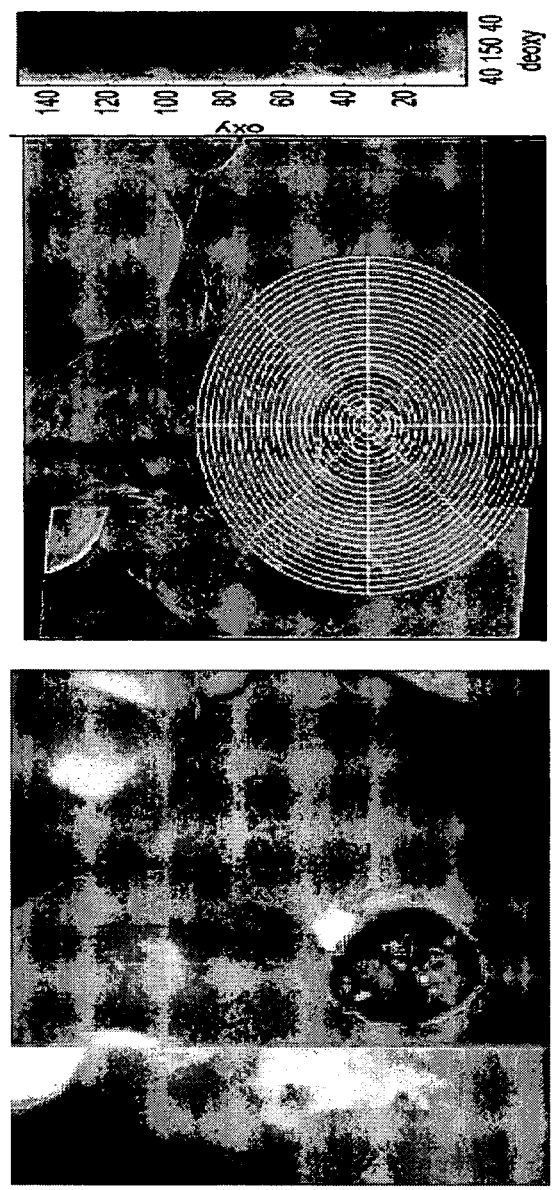
FIG. 5. The regions of ulcer extension (non-healing set) provide a surrogate for definition of tissue at risk in a foot with unbroken skin.

A radial map analysis routine is used for evaluating sites with ulcers. The radial maps reduce the hyperspectral image data into mean oxyHb and deoxyHb values measured at 200 separate locations around the ulcer. In this way different tissue regions can be compared and tissue immediately adjacent to the wound margin can be assessed and compared to tissue that is further away. Typically measurements within the wound are avoided due to the exudates that interfere with the measurement. The individual segments can be used to identify regions that surround a healing ulcer from those that surround an ulcer that is not healing or extending. (FIG. 5).

We applied this radial profile methodology to examine our data from a study in which 10 diabetic subjects with 17 ulcers were enrolled. Twenty-one separate radial maps were performed on the 17 ulcers. Of the 21 separate ulcer locations, 14 were reported to heal clinically while 7 did not heal clinically. An increase in oxyHb and deoxyHb was noted when using a linear mixed model of hyperspectral tissue oxygenation values determined in tissue surrounding the ulcer (Table Below). Interestingly, the percent hemoglobin oxygen saturation did not differ between the two groups suggesting that the blood supply is meeting the oxygen demands for the healing ulcer by increasing the amount of blood delivered to the wound while no response is noted for the nonhealing ulcers because the nonhealing ulcer is not communicating with the systemic circulation.

Linear mixed effects model results of tissue oxygenation values in tissue surrounding an ulcer.

|  | Group Estimates (±SEM) | | Mean (±SEM) | |
|---|---|---|---|---|
| MHT | Not Healing | Healing | p-value | Control Foot |
| oxyHb | 36.4 ± 2.2 | 51.9 ± 1.8 | <.0001 | 53.2 ± 0.7 |
| deoxyHb | 34.2 ± 1.9 | 47.8 ± 1.6 | <.0001 | 47.7 ± 0.5 |
| O$_2$-sat | 0.51 ± 0.01 | 0.51 ± 0.01 | 0.8646 | 0.514 ± 0.004 |

A simple algorithm was deduced from the linear mixed effects model results. Namely if the mean value of oxyHb determined from tissue surrounding a wound is larger than 45, the ulcer is predicted to heal while if the value is less than 45 the ulcer is predicted to not heal. Using this algorithm, 6 of the 7 (sensitivity=86%) clinically nonhealing ulcers were predicted to not heal while 12 of the 14 clinically healing ulcers were predicted to heal (specificity=86%). A scatterplot of these results are shown in FIG. 2.

The results of these analyses conclude

HT showed significant differences in hyperspectral tissue oxygenation measurements between ulcers that healed and ulcers that did not heal.

These results indicate that increased oxygen delivery to the ulcer area is associated with an increased healing rate.

HT identifies microvascular abnormalities in the diabetic foot and provides early information regarding the healing capacity of diabetic foot ulcers. This information can assist in managing foot ulceration, and predict outcomes.

Inherent in the radial profile analysis was the definition of areas of "tissue at risk" not originally adjacent to the ulcer that then went on over the six month period to ulcerate.

We have compared HT foot images to current and past clinical measurements in the patient's clinical history. We also contrasted the HT images of subjects with and without ulcers, and contrast the feet of subjects with one ulcerated foot and one ulcer-free foot. This determined which features and summary variables of HT tissue oxygenation maps correlate with ulceration and risk factors related to ulceration. Patients with existing peripheral vascular disease were evaluated clinically in terms of symptoms (claudication, rest pain), tissue loss, other vascular lab studies (ankle-brachial index, transcutaneous oxygen tension, neuropathy symptom score pulse volume recording and laser Doppler iontophoresis, LDI), and using hyperspectral imaging.

In addition, establishing a broad spectral library has enabled us to determine a baseline for assessing diabetic foot problems and other tissue problems in a broad group of people with diabetes. Many other factors could potentially modify the nature of HT spectral signatures. We have assessed how age, skin color, and disease duration correlate with HT features. We have determined how other demographic and anthropomorphic variables correlate with HT features.

HT better predicts healing potential of skin wounds and amputation sites than other available techniques especially in diabetics. In this group of patients we commonly find lower extremity skin lesions in the form of ulceration despite the presence of palpable pulses or adequate flow by conventional vascular lab studies. This technique assesses perfusion at the skin level to find out that whether despite palpable pulses, the formation of ulcers is due to microcirculatory changes or skin islands of ischemia.

There are many methods of orthotics known to one of skill in the art. Pressure sensitive mats, or gels, or gel shoe inserts can be used. Orthotics can be specially tailored to properly redistribute pressures on the basis of HT gradient map and/or pressure.

Foot Contouring

1.) PedAlign—infrared optical scanner that measures the shape of the foot including foot contours and arch height measurements and contour and uses this information when designing custom orthotics. Orthotics are composed of semi-rigid polypropylene or graphite composite shells with different heal cup depths.
2.) Casting—plaster casts or foams that remember the shape of the foot when stepped on.

It should also be understood that the use of HT maps and index measurements created by the combination of HT maps or other metrics of tissue oxygenation and perfusion and pressure measurements combined with HT maps or other metrics of tissue oxygenation and perfusion is not limited to the sole of the foot or feet, but also to limbs, amputee limbs, or other extremities and areas of tissue of the body of interest.

HT maps are evaluated independently or paired with any of the following data: past medical history, past surgical history, medications, physical examination, ankle/brachial indices (ABIs), TcPO2, and pulse volume recording (PVR).

The HT maps are then evaluated independently or compared with degree of clinical disease and level of perfusion to determine. Combination of HT data with ankle brachial index, pulse volume recording, duplex scan, angiogram, MRA images and/or transcutaneous oxygen tension measurements may also be undertaken to determine the level of perfusion and oxygenation at the skin level. Finally, for patients undergoing revascularization, pre and post-operative images may be compared to determine if there is a change in the level of perfusion at the skin level. HT studies may be performed with and without exercise to enhance information about tissue perfusion and islands of ischemia.

As embodied and broadly described here, the present invention is directed to a process for directly measuring pressure and the characteristics of tissue health related to adequacy of perfusion and as can be described by metrics of tissue oxygenation including oxygen delivery, oxygen extraction and oxygenation in the foot of diabetic and non-diabetic patients and in other tissues of the body subjected to pressure.

Charcot foot disease is known as a neuropathic osteoarthropathy and can be observed in diabetics. The exact etiology is still unknown; however, the most common theory involves hyperperfusion of the foot. The autonomic component of the neuropathy leads to vasodilatation and hyperperfusion. The perfusion causes demineralization of the bones. Weight bearing forces cause the bones to begin to fragment and fracture, leading to collapse of the arch. The long-term sequelae of a rockerbottom-shaped foot leads to high-pressure areas that are prone to ulceration.

Charcot ulcerations are typically mechanical in nature but can become infected within the soft tissue and osseous structures. A midfoot collapse with tissue loss and radiographic signs of osteomyelitis in addition to clinical signs of edema and erythema often lead to a confusing and difficult-to-diagnose condition. Charcot osteoarthropathies often are diagnosed as an osteomyelitis by plain radiographs. Scintigraphic studies help in determining the nature of these changes.

The present invention provides a combination of information regarding pressure exerted on the foot while standing or walking with information about perfusion of the foot is obtained by thermal imaging, hyperspectral imaging (HT), duplex scanning, angiography, MRA or laser Doppler imaging and provides a map and perfusion of the foot. This map is translated into maximal protection of the foot. This concept can be translated into the assessment and protection of other tissues and body parts. In one embodiment the combined data is transferred to an orthotic manufacturing device which utilizes digital information to create the desired contour.

One embodiment combines a HT map with digitized information regarding the pressure measured from the foot or other tissue of the body while it is weight bearing. Using image registration techniques, an index map is created which combines oxygenation and pressure information according to an algorithm that permits the construction of an orthotic, prosthetic or cushion which then delivers less pressure to the foot or other tissue in regions of decreased oxygenation. This algorithm modifies the standard construction of the orthotic or cushion with a factor which changes it from providing even distribution of pressure to less pressure where tissue oxygenation is compromised.

Hyperspectral technology offers the ability to directly measure tissue damage, or clearly related biomarkers related to tissue damage, rather than merely parameters indirectly related to it. Otherwise stated, foot tissue that is poorly perfused or metabolically unstable is more susceptible to the effects of pressure on the region.

A hyperspectral tissue map which provides information relative to the oxyHb and deoxyHb present in tissue in the region of interest on a pixel by pixel basis has been created and applied to the assessment of diabetic feet with and without foot ulceration.

Such a map of the perfusion and metabolism of the tissue (reflecting oxygen delivery and oxygen extraction), helps us to provide information concerning what tissue will heal and what tissue is at risk for ulceration. In one embodiment, this HT map is paired with a spatial map of the pressure exerted by the weight of the patient and/or the pressure between the tissue and a shoe surface to provide a composite image that would indicate areas where pressure needed to be minimized to prevent ulceration in a region at particular risk.

HT measurements taken after walking in particular foot wear or with a prosthetic or orthotic could demonstrate areas of subclinical tissue damage on either platar or dorsal foot surfaces or on amputation stump due to shear stress and guide orthotic or prosthetic or footwear remodeling.

In one embodiment, HT measurements of venous ulcers guide the selection of pressure to be applied. This would be especially important in the case of mixed arterial and venous ulcers. In one embodiment, HT measurements could be taken of the distal portions of the extremity through a transparent wrap during venous compression therapy. In another embodiment, HT measurements could help guide the selection of compression strength based on evaluation of arterial or ischemic disease and potential islands of ischemia.

In the case of a wound, HT maps could be used to guide the application of negative pressure therapy in both location and degree based on the assessment of both the wound and the surrounding tissue. HT maps could be used prior to application of negative pressure or through a transparent material during therapy to assess the effects on the tissue during therapy.

In another embodiment, a mask/optically clear window is used to analyze perfusion while changing pressure. The window can be static in either a flat or conformal shape, or dynamic varying based either on exerted pressure or some other control schema. It can also provide temperature variation (make the tissue hot or cold) or vibration to enhance circulation. A combination of all of these occurring across a surface in contact with the tissue can also occur.

Such a method is also applied to situations of other orthotic appliances such as amputation prostheses or the treatment of decubiti or other wounded areas. A variety of forms including imaging of the patient while reclined, taking images of the top, bottom and soles of the feet and a pressure measurement while standing on a special plate or walking in special shoes or boots to record pressure over different regions of tissue are used. A hyperspectral image taken through a transparent plate incorporates the effects of pressure on the tissue while the patient is standing.

In another embodiment, a hyperspectral image with the patient lying down and no pressure on the foot with one taken with the patient standing, or one taken immediately after walking is performed. Other uses include performing the HT in free flight/fall, such as space. Also, it is used to assess the degree of healing and functionality of therapy for severely burned patients where you need to adjust the mask/bandage on the tissue. Other uses include using in a hospital bed adjustment, overlying pad on bed, or wound suction device adjustment as in the VAC Freedom™ device (Kinetics Concepts, Inc.).

In another embodiment, liquid crystals are used for mapping the pressure detected on the foot. A thin film filled with viscous fluid is provided. The patient steps on the film applying pressure from body weight. The high pressure areas push the fluid out, causing the high pressure areas to appear transparent. The low pressure areas are filled with fluid.

Other uses for this system also includes a means of measuring tissue healing and/or rate of progression of infection through tissue, an application for measurement of effectiveness of a tourniquet, determining proper fit of clothing such as brassieres, gas masks, shock absorbing plates for body armor, etc, measurement of absorption of trans-dermal drugs into tissue, both instantaneous and time release, measurement of fit of airline seats, wheel chairs, etc. to look at impact (deep vein thrombosis, bed sores, etc.), measurement of fit of boots/shoes to avoid blisters and the fit of riding tack on horses to reduce blisters, passive biometric ID through mapping of unique vascular structure non-invasively, and measurement of response to toxins, such as anaphylactic shock, prior to full onset and seizures or respiratory distress.

Image registration could be facilitated by the use of proprietary fiducial marks and proprietary registration software. Calibration could be facilitated by proprietary calibrators or calibration routines.

Other embodiments and uses of the invention will be apparent to those skilled in the art from consideration of the specification and practice of the invention disclosed herein. All references cited herein, including all patents and publications for what ever reason, are specifically and entirely incorporated by reference. The specification and examples should be considered exemplary only with the true scope and spirit of the invention embodied within the following claims.

HT Procedure

A baseline HT measurement of the forearm is required as a part of each examination to provide data regarding the systemic microcirculation. In the lower extremity, HT measurements are taken at different sites to assess the location and severity of regional ischemic disease and local microvascular changes.

The patient is positioned on the examining table in such a way as to expose and stabilize the areas to be studied. The operator enters patient information into the machine and calibrates the HT equipment by placing the "Calibration Check Pad" in its holder and taking a measurement from the "Calibration Check Pad" to ensure appropriate calibration, focus and correction for background lighting.

The forearm site is generally the first to be studied. An HT "Measurement Check Target" (7 mm pad with hydrogel backing) is placed on the patient's forearm. The instrument head is adjusted until the focusing beams converge on the target. A data set from a 10 cm×13 cm region is then acquired by the operator over a 15 second interval. The data collected from the tissue region is presented as a map of the tissue on the monitor for inspection by the operator. Quantitative measurements of oxyhemoglobin (HT COM-Oxy), deoxyhemoglobin (HT COM-Deoxy, and oxygen saturation (HT COM-Sat) over the central area of the tissue region is displayed on a computer screen along with a colorized tissue map reflecting the HT COM-Oxy and the HT COM-Deoxy levels. The operator then obtains additional quantitative data from specific region(s) of interest within the area examined (e.g., around an ulcer).

The operator repeats the steps (other than calibration) above for each additional site: (e.g. the dorsum (top) of the foot, the plantar surface (sole) of the foot, the calf, an ulcer). The quantitative oxygenation measurements obtained for each site are recorded along with the colorized tissue maps. The operator saves the data collected and the maps displayed on the screen to the instrument's hard drive to record the quantitative HT measurements along with the location from which they were derived. These sites provide information about local, regional, and systemic effects on tissue oxygenation in the lower extremity.

The physician reviews and interprets a print out of the maps of the tissue and the quantitative tissue oxygenation measurements for each site. This review includes additional regions of interest selected by the operator and/or the physician within a data collection area. The physician compares HT measurements from multiple collection sites in order to obtain information on systemic, regional and local microvascular pathophysiology. The physician may also review HT maps stored on the computer to obtain additional oxygenation measurements from any other regions of interest which may be identified during his review in order to complete his/her review and interpretation.

The physician also may review previous studies and the HT data from the current analysis with HT measurements obtained during previous sessions. The physician documents and records his/her interpretation in the patient's medical record and sends a report describing the findings to the referring physician.

HT Clinical Applications:

HT provides quantitative and anatomically relevant information about local tissue condition. HT oxygenation measurements reflect the summation of effects of systemic microvascular disease, regional macrovascular disease and local tissue pathophysiology (i.e. response to wounding). Given its capabilities for providing quantitative information related to tissue oxygenation (oxygen delivery and oxygen extractions), HT can be useful in the following settings:

Predict healing in diabetic foot ulcers by using the correlation of degree of tissue oxygenation with healing (HT COM-Oxy>45 associated with healing and <45 associated with non-healing)[56, 61]

Deliver information about the progression of microcirculatory disease in diabetes by demonstrating lower levels of tissue oxygenation in the feet and forearms of diabetics afflicted with more advanced disease Define the presence and quantitate the severity of neuropathy Provide an early demonstration of claudication and islands of ischemia which to identify those patients requiring earlier angiographic evaluation and intervention Provide a tool for diagnosis and directing treatment of critical limb ischemia Identify smaller regions of ischemia, provide a quantitative metric for their assessment and track their response to therapy Provide an assessment of tissue viability relevant in making decisions as to when and where to amputate Provide information as to adequacy of tissue oxygenation around a wound to help the physician determine safety of debridement, avoid debridement of an ischemic region and refer for vascular evaluation re intervention when necessary Provide information to help define tissue at risk for ulceration and initiate a prevention program (i.e. skin care, orthotics, vascular evaluation, elective foot surgery to improve biomechanics)

Direct off-weighting including accommodative orthotic device or shoegear to reduce pressure and treat or prevent ulceration Assist in the timing and level of amputation Assist in the assessment of adequacy of tissue oxygenation after interventional stent placement or surgical distal bypass Assist in the assessment of steal phenomenon in AV fistulas placed for use in dialysis of chronic renal failure patients Provide a screening tool to evaluate viability of tissue for use in surgical flaps prior to reconstruction or amputation Assist in assessing whether early surgical intervention is needed to reduce pressure (prophylactic surgery)

Provide a screening tool for pre-operative assessment (which provides better information than ABIs) for diabetes patients prior to elective surgery Provide a general screening tool for tissue oxygenation assessment with the capability of summing effects of local, regional and systemic disease in an anatomically relevant fashion (which may become as standard as checking pulses and sensation for all patients with diabetes)

Deliver information about systemic physiology and metabolism in hemorrhagic shock and hypovolemic decompensation useful in the early determination of hemodynamic compromise and impending shock[44]

HT is useful clinically because it measures local tissue oxygenation based upon the total as well as relative pathophysiologic contributions of systemic, regional and local macro- and micro-vascular pathology to local tissue damage. HT measures both oxygen delivery to and oxygen extraction by tissue in an anatomically relevant format, producing a colorized map of the area of tissue being studied. Within the HT tissue map, every pixel contains information regarding oxyhemoglobin and deoxyhemoglobin levels and oxygen saturation. The HT map displays the amount of tissue oxygenation throughout the area being assessed with a spatial resolution of 100 microns. This localized and quantitative information about tissue oxygenation can be used to assist in the evaluation of ischemic tissue or other damaged tissue such as that around a wound.

Currently, no other tests provide the information delivered by HT COM. Other non-invasive tests have fallen short of providing actionable information.

One group of tests (e.g. duplex scan) primarily assess large vessel disease and the level of an obstruction to flow, but do not provide information about the effects of such an obstruction on specific tissue regions. Unlike HT COM, these tests provide no information about the contribution of microvascular disease to the pathophysiology and no information as to the adequacy of perfusion.

A second group of tests, such as transcutaneous oxygen monitoring, do not provide the same level of anatomic localization as HT COM, do not assess the adequacy of the circulation, and cannot be applied successfully to regions on the plantar surface of the foot or regions that are not flat or that are near a wound.

A third group of tests which include pulse volume recordings and ankle brachial indices are inaccurate in the presence of calcified vessels, whereas HT measurements are not affected by the presence of calcification of the macrovascular tree.

HT delivers information assessing the impact of both macrovascular and microvascular disease on the tissue being evaluated. HT is a clinical alternative to other non-invasive physiologic studies of the arterial system. It provides more reliable, more anatomically relevant, and more specific information about the oxygenation of tissue and general physiologic state than the currently performed procedures (non-invasive physiologic studies of upper or lower extremity arteries, single level, bilateral or non-invasive physiologic studies of upper or lower extremity arteries, multiple levels or with provocative functional maneuvers, complete bilateral study). For example, no other technology other than HT provides a complete assessment as to whether the microcirculation and oxygenation status of the tissue surrounding a diabetic's ulcer or wound is adequate to meet the physiologic needs for healing). Examples include diabetic foot ulcers, neuropathic foot ulcers, ischemic ulcers, stasis [venous] ulcers, sacral ulcers, symptomatic arterial insufficiency, diabetic microvascular disease, trauma to the extremities, tissue viability after attempted revascularization, tissue flaps, burns, and post-debridement tissue viability.

HT is a more versatile measurement of tissue oxygenation than TCPO2:

Providing anatomically relevant data of the specific tissue region under evaluation with high spatial resolution Providing data from locations in which TCPO2 cannot be used (the foot sole or areas around a wound), Delivering data that is not rendered inaccurate by small area of sampling by the TCPO2 probe which does not take into account tissue heterogeneity Delivering data of skin under normal conditions and not after high temperature induced vasodilatation used in the TCPO2 technique Preventing operator errors by the technician related to the more complex procedures required for proper TCPO2 probe siting and application vs turnkey HT scan Delivering more relevant information which sums the contributions of local, regional and systemic disease and is not rendered inaccurate by hardening or inelasticity of peripheral vessels a better metric of HT measurements have relevance in the assessment of the following conditions:

HT is more relevant that ABI or PVR in reporting local, anatomically relevant information in elderly and diabetic patients with calcified or inelastic vessels:

Providing information about specific tissue regions

Providing an indication of oxygen extraction and the adequacy of perfusion or oxygen delivery Providing information that is much easier and quicker to collect and less operator dependent Instrumentation In one embodiment there is a methodology to integrate components of existing contour measuring devices designed to deliver uniform pressure to the foot via an orthotic with a hyperspectral technology map to provide information to modify the creation of the orthotic to incorporate information relative to tissue oxygenation so that "the least pressure can be placed on the tissue most at risk". One embodiment requires the construction of a novel device which encorporates aspects of both parent devices. To achieve data fusion it is necessary to coregister data from the HT map and whatever contour or pressure measuring technology is chosen, here described for the Pedalign PMI system.

The process of coregistration depends on the level of integration between both instruments. The following are three possible forms of integration:

1) Both instruments are assembled as a single unit and mounted rigidly with respect to each other as well as stepping platform. They have overlapping fields of view and the measurements are conducted simultineously.

In this case the fields of view can be coregistered during the process of the instrument integration using special calibrator. This calibrator will consist of a rectangular pattern of small rubber pads pressured against the stepping platform. The property of this calibrator is that it can produce an image of rectangular pattern visible in both PMI and FootVu data. After numerical processing of the corresponding data from the both instruments the transformation algorithm will be obtained. When applied to the consequently measured FootVu data this algorithm will compansate for effects of parallax, scaling and rotational factors and precisely coregister FootVu data with the data from PMI.

2) The instruments are manufactured as separate units but can measure data from the same stepping platform simultaneously. In this case the coregistration can be achieved based the contour of the area where foot skin touches the platform. This contour is easily detectable both on PMI and FootVu images. By feeding both images to the special numerical coregistration procedure which will deduce the "touching contours" the transformation algorithm will be derived. Just like in the previous case, this algorithm will modify the FootVu data to make the image to be coregistered with PMI data.

3) In the case when the instrument units are not intergrated and measurements by PMI and FootVu are taken separately fiduciary registration marks will be used. These marks are four small circular pads which can be applied to the foot close to the edges of the area registered in both PMI and FootVu data. The position of these pads will not change between PMI and FootVu measurements. By locating the positions of these pads on the corresponding PMI and FootVu images the special numerical procedure will derive the transformation algorithm which will be then applied to FootVu image to achieve coregistration.

Application of similar principles for different measurements of pressure or tissue assessment with HT mapping should be obvious to those skilled in the art.

EXAMPLES

A correlation has been established between HT data and clinical disease in diabetes and in peripheral vascular disease. Patients with existing peripheral vascular disease were evaluated clinically in terms of symptoms (claudication, rest pain), tissue loss, conventional vascular lab studies (ABI, transcutaneous oxygen tension, toe pressures), and using hyperspectral imaging. The HT data was analyzed in conjunction with the other data, and a correlation with severity of disease determined.

In diabetic foot disease we have compared this technology to other available techniques that evaluate extremity perfusion: ankle brachial index, pulse volume recording, transcutaneous oxygen tension, and toe pressures. HT has been shown to better predict healing potential of skin wounds in diabetics, with a sensitivity of 86% and a specificity of 86%. In this group of patients we commonly find lower extremity skin lesions in the form of ulceration despite the presence of palpable pulses or adequate flow by conventional vascular lab studies. This technique includes the influences of systemic microvascular and local factors in its assessment of the adequacy of oxygenation at the skin level to define where, despite palpable pulses, the formation of ulcers is likely to occur, and demonstrates islands of ischemia, and differences along angiosomes. This demonstration of islands of ischemia can be obtained in some instances at rest and in some cases appears after exercise. These underperfused regions can be defined as regions of tissue at risk that warrant protection from pressure or shear stress.

HT mapping can evaluate patients after endovascular or operative revascularization. Vascular bypasses reconstruct major named vessels that can be evaluated by detection of blood flow in the bypassed arteries; but the perfusion at the skin level cannot be easily or accurately evaluated. This technique offers an opportunity to do so. HT data offers the greatest benefit as an early indicator of the risk of foot ulcers. This allows the physician to adjust the treatment plan to prevent or delay the occurrence of an ulcer.

In another embodiment, the present invention performs HT on tissue under the circumstances of wound healing with and without arterial occlusion in the ear of diabetic or non-diabetic rabbits. In this circumstance, HT can track wound healing and identify and quantify the angiogenesis and effects of EPCs on wound healing. The spectra of tissue oxy and deoxy hemoglobin and the calculated tissue oxygen saturation reflect the oxygen delivery, oxygen extraction and metabolic state of tissue. These HT maps could be useful in designing or tailoring surfaces or devices to optimize the pressure to the healing surface. This could be by providing zero pressure, a specified amount of positive pressure or negative pressure to different regions of tissue to optimize healing or prevent breakdown. Using spectral features, NIR hyperspectral imaging has been used to visualize otherwise undetectable variations in tissue perfusion and predict tissue viability following plastic surgery long before they can be determined clinically.[47] End tissue of a long pedicle flap in the rat that has insufficient oxygenation to remain viable is readily apparent in these local tissue maps calculated from NIR images acquired immediately following surgery. By contrast, visible clinical signs of impending necrosis do not become apparent for 12 hours after surgery. The compromised tissue goes on to slough 72 hours later.

In another embodiment, hyperspectral technology is used to assess human subjects under circumstances of hemodynamic compromise. Here the whole body is compromised and the this embodiment speaks to the design of beds or cushions for patients with shock or low flow.

REFERENCES

1. Boyko E J, Ahroni J H, Stensel V, Forsberg R C, Davignon D R, Smith D G. A prospective study of risk factors for 1. diabetic foot ulcer. The Seattle Diabetic Foot Study. Diabetes Care 1999; 22(7):1036-42.
2. Edelman D, Sanders L J, Pogach L. Reproducibility and accuracy among primary care providers of a screening examination for foot ulcer risk among diabetic patients. Prev Med 1998; 27(2):274-8.
3. Rith-Najarian S J, Stolusky T, Gohdes D M. Identifying diabetic patients at high risk for lower-extremity amputation in a primary health care setting. A prospective evaluation of simple screening criteria. Diabetes Care 1992; 15(10):1386-9.
4. Ramsey S D, Newton K, Blough D, McCulloch D K, Sandhu N, Reiber G E, et al. Incidence, outcomes, and cost of foot ulcers in patients with diabetes. Diabetes Care 1999; 22(3):382-7.
5. Reiber G E, Boyko E J, Smith D C. Lower extremity foot ulcers and amputations in diabetes. In: Harris, Cowie, Stem, Boyko E J, Reiber G E, Bennet, editors. Diabetes in America. 2nd ed. Washington, D.C.: US Government Printing Office; 1995. p. 402-428.
6. Frykberg R G, Lavery L A, Pham H, Harvey C, Harkless L, Veves A. Role of neuropathy and high foot pressures in diabetic foot ulceration. Diabetes Care 1998; 21(10):1714-9.
7. Sumpio B E. Foot ulcers. N Engl J Med 2000; 343(11): 787-93.
8. Young M J, Breddy J L, Veves A, Boulton A J. The prediction of diabetic neuropathic foot ulceration using vibration perception thresholds. A prospective study. Diabetes Care 1994; 17(6):557-60.
9. Cavanagh P, Young M, Adams J, al. e. Correlates of structure and function in neuropathic diabetic feet. Diabetologia 1991; 34(Suppl 2):A39 (abstract).
10. Lavery L A, Armstrong D G, Vela S A, Quebedeaux T L, Fleischli J G. Practical criteria for screening patients at high risk for diabetic foot ulceration. Arch Intern Med 1998; 158(2): 157-62.
11. McMillan D E. Development of vascular complications in diabetes. Vasc Med 1997; 2(2):132-42.
12. Arora S, Smakowski P, Frykberg R G, Simeone L R, Freeman R, LoGerfo F W, et al. Differences in foot and forearm skin microcirculation in diabetic patients with and without neuropathy. Diabetes Care 1998; 21(8):1339-44.
13. Novo S. Classification, epidemiology, risk factors, and natural history of peripheral arterial disease. Diabetes Obes Metab 2002; 4 Suppl 2:S1-6.
14. Hittel N, Donnelly R. Treating peripheral arterial disease in patients with diabetes. Diabetes Obes Metab 2002; 4 Suppl 2:S26-31.
15. Stevens M J, Feldman E L, Greene D A. The aetiology of diabetic neuropathy: the combined roles of metabolic and vascular defects. Diabet Med 1995; 12(7):566-79.
16. Parkhouse N, LeQueen P M. Impaired neurogenic vascular response in patients with diabetes and neuropathic foot lesions. N Engl J Med 1988; 318: 1306-1309.
17. Arora S, Pomposelli F, LoGerfo F W, Veves A. Cutaneous microcirculation in the neuropathic diabetic foot improves significantly but not completely after successful lower extremity revascularization. J Vasc Surg 2002; 35:501-505.
18. Hughes R, Rowlands H, McMeekin S. A laser plantar pressure sensor for the diabetic foot. Med Eng Phys 2000; 22(2):149-54.
19. Rhodes G R, Cogan F. "Islands of ischemia": transcutaneous PtcO2 documentation of pedal malperfusion following lower limb revascularization. Am Surg 1985; 51(7): 407-13.
20. Sangeorzan B J. Amputations within the foot. Management of the dysvascular lower limb by the amputee clinic team. In: Special team for amputations, mobility, and prosthetics/orthotics conference Mar. 14-16, 1990; Seattle, Wash.
21. Friedman L W. Rehabilitation of the lower extremity amputee. Philadelphia: W.B. Saunders Co; 1990.
22. Stratonnikov A A, Loschenov V B. Evaluation of blood oxygen saturation in vivo from diffuse reflectance spectra. J Biomed Opt 2001; 6(4):457-67.
23. Knoefel W T, Kollias N, Rattner D W, Nishioka N S, Warshaw A L. Reflectance spectroscopy of pancreatic microcirculation. J Appl Physiol 1996; 80(1):116-23.
24. Kollias N. The physical basis of skin color and its evaluation. Clin Dermatol 1995; 13(4):361-7.
25. Kollias N, Gillies R, Muccini J A, Uyeyama R K, Phillips S B, Drake L A. A single parameter, oxygenated hemoglobin, can be used to quantify experimental irritant-induced inflammation. J Invest Dermatol 1995; 104(3):421-4.
26. Kollias N, Baqer A. Spectroscopic characteristics of human melanin in vivo. J Invest Dermatol 1985; 85(1):38-42.
27. Kollias N, Baqer A H. Absorption mechanisms of human melanin in the visible, 400-720 nm. J Invest Dermatol 1987; 89(4):384-8.
28. Takiwaki H. Measurement of skin color: practical application and theoretical considerations. J Med Invest 1998; 44(3-4):121-6.
29. Sowa M G, Mansfield J R, Jackson M, Docherty J C, Deslauriers R, Mantsch H H. FT-IR/NIR assessment of ischemic damage in the rat heart. Mikrochimica Acta 1997; 14(Supp):451-453.
30. Doornbos R M, Lang R, Aalders M C, Cross F W, Sterenborg H J. The determination of in vivo human tissue optical properties and absolute chromophore concentrations using spatially resolved steady-state diffuse reflectance spectroscopy. Phy Med Biol 1999; 44(4):967-981.
31. Zonios G, Bykowski J, Kollias N. Skin melanin, hemoglobin, and light scattering properties can be quantitatively assessed in vivo using diffuse reflectance spectroscopy. J Invest Dermatol 2001; 117(6):1452-1457.
32. Bassi D, Kollias N, Fernandez-del Castillo C, Foitzik T, Warshaw A L, Rattner D W. Impairment of pancreatic microcirculation correlated with the severity of acute experimental pancreatitis. J Am Coll Surg 1994; 179(3): 257-263.
33. Kollias N, Gillies R, Muccini J A, Phillips S B, Drake L A. Oxyhemoglobin is a quantifiable measure of experimentally induced chronic tretinoin inflammation and accommodation in photodamaged skin. Skin Pharmacol 1997; 10(3):135-143.
34. Toas Y, Kollias N, Lee W P, May J W, Jr Reduction of ischemia-reperfusion injury by monoclonal antibody to intercellular adhesion molecule-1. Transplant Proc 1996; 28(3):1210-1211.
35. Kollias N, Baqer A, Sadiq I, Sayre R M. In vitro and in vivo ultraviolet-induced alterations of oxy- and deoxyhemoglobin. Photochem Photobiol 1992; 56(2):223-7.
36. Sowa M G, Matas A, Schattka B J, Mantsch H H. Spectroscopic assessment of cutaneous hemodynamics in the presence of high epidermal melanin concentration. Clinica Chimica Acta 2002; 317(1-2):203-212.
37. Canvin J M, Bematsky S, Hitchon C A, Jackson M, Sowa M G, Mansfield J R, et al. Infrared spectroscopy: shedding light on synovitis in patients with rheumatoid arthritis. Rheumatology (Oxford) 2003; 42(1):76-82.

38. McIntosh L M, Summers R, Jackson M, Mantsch H H, Mansfield J R, Howlett M, et al. Towards non-invasive screening of skin lesions by near-infrared spectroscopy. J Invest Derrnatol 2001; 116(1):175-81.
39. Bowles J H, Antoniades J A, Baumback M M, Grossmann J M, Haas D, Palmadesso P J, et al. Real-time analysis of hyperspectral data sets using NRL's ORASIS algorithm. In: Descour M R, Shen S S, editors. Imaging Spectrometry III; 1997: Proc SPIE 1997. p. 38-45.
40. Riaza A, Strobl P, Muller A, Beisl U, Hausold A. Spectral mapping of rock weathering degrees on granite using hyperspectral DAIS 7915 Spectrometer Data. Inteml J Applied Earth Observation and Geoinformation Special issue: Applications of imaging spectroscopy 2001; 3-4: 345-354.
41. Thenkabail P S, Smith R B, De Pauw E. Hyperspectral vegetation indices and their relationships with agricultural crop characteristics. Remote Sens Environ 2000; 71(REMOTE SENS ENVIRON):158-182.
42. Tran C D. Development and analytical applications of multispectral imaging techniques: an overview. Fresenius J Anal Chem 2001; 369(3-4):313-9.
43. Colarusso P, Kidder L H, Levin I W, et al. Infrared spectroscopic imaging: from planetary to cellular systems. Appl Spectrosc 1998; 52:106A-120A.
44. Greenman R I, Panasyuk S, Wang X, Lyons T E, Dinh T, Longorio L, et al. Early changes in the skin microcirculation and muscle metabolism of the diabetic foot. Lancet 2005; 366:1711-1718.
45. Zuzak K J, Schaeberle M D, Gladwin M T, Cannon R O, 3rd, Levin I W. Noninvasive determination of spatially resolved and time-resolved tissue perfusion in humans during nitric oxide inhibition and inhalation by use of a visible-reflectance hyperspectral imaging technique. Circulation 2001; 104(24):2905-10.
46. Treado P J, Morris M D. Infrared and Raman spectroscopic imaging. Appl Spectrosc Rev 1994; 29:1-38.
47. Payette J R, Sowa M G, Germscheid S L, Stranc M F, Abdulrauf B, Mantsch H H. Noninvasive diagnostics: predicting flap viability with near-IR spectroscopy and imaging. Am Clinical Laboratory 1999; 18:4-6.
48. Mansfield J R, Sowa M G, Payette J R, Abdulrauf B, Stranc M F, Mantsch H H. Tissue viability by multispectral near infrared imaging: a fuzzy C-means clustering analysis. IEEE Trans Med Imaging 1998; 17(6):1011-8.
49. Gillies R, Freeman J E, Cancio L C, Brand D, Hopmeier M, Mansfield J R. Systemic effects of shock and resuscitation monitored by visible hyperspectral imaging. Diabetes Technol Therapeut 2003; 5(5):847-855.
50. Morag E, Cavanagh P R. Radiographic and ultrasonic methods to study foot structure. In: Third Symposium on Footwear Biomechanics, Session 4; 1997; Tokyo; 1997.
51. Stevenson J M, Bossi L L, Bryant J T, Reid S A, Pelot R P, Morin E L. A suite of objective biomechanical measurement tools for personal load carriage system assessment. Ergonomics 2004; 47(11):1160-79.
52. Dawes-Higgs E K, Swain M V, Higgs R J, Appleyard R C, Kossard S. Accuracy and reliability of a dynamic biomechanical skin measurement probe for the analysis of stiffness and viscoelasticity. Physiol Meas 2004; 25(1):97-105.
53. Wang J, Brienza D M, Yuan Y, Karg P, Xue Q. A compound sensor for biomechanical analyses of buttock soft tissue in vivo. J Rehabil Res Develop 2000; 37(4).
54. Bocobo C R, Castellote J M, MacKinnon D, Gabrielle-Bergman A. J Rehabil Res Develop. Videofluoroscopic evaluation of prosthetic fit and residual limbs following transtibial amputation 1998; 35(1):6-13.
55. Madsen M T, Haller J, Commean P K, Vannier M W. A device for applying static loads to prosthetic limbs of transtibial amputees during spiral CT examination. J Rehabil Res Develop 2000; 37(4).
56. Dinh T, Panasyuk S V, Jiang C, Freeman J, Panasyuk A A, Nemey M, et al. The use of medical hyperspectral imaging (MHSI) to evaluate microcirculatory changes in diabetic foot ulcers and predict clinical outcomes. Oral 106-OR at the American Diabetes Association 66th Scientific Session Jun. 10, 2006, Washington, D.C. Diabetes 2006; 55(S1): A25.
57. Veves A, Khaodhiar L, Panasyuk L, Jiang C, Freeman J, Panasyuk A, et al. The use of medical hyperspectral imaging (MHSI) to evaluate microcirculatory changes and predict clinical outcomes: application to diabetic foot ulcers. Poster P-16 at the Society of Vascular Medicine and Biology 17th Annual Scientific Session, May 2006, Philadephia, Pa. Vascular Medicine 2006; 11(S1):S7.
58. Akbari C M, Saouaf R, Barnhill D F, Newman P A, LoGerfo F W, Veves A. Endothelium-dependent vasodilatation is impaired in both micro- and macrocirculation during acute hyperglycemia. J Vasc Surg 1998; 28:687-694.
59. Caballero A E, Arora S, Saouaf R, Lim S C, Smakowski P, Park J Y, et al. Micro- and macro-vascular reactivity is impaired in subjects at risk for type 2 diabetes. Diabetes 1999; 48:1863-1867.
60. Caselli A, Singh B D, O'Connor C, Shah C, Veves A. Assessment of laser perfusion imager's in vivo reliability: Can it be used for a prospective analysis? J Laser Applic 2002; 14:198-202.
61. Dinh T, Panasyuk S, Freeman J, Panasyuk A A, Lew R, Brand D, et al. Medical hyperspectral imaging (MHSI) evaluation of microcirculatory changes to predict clinical outcomes: Application to diabetic foot ulcers. Society of Vascular Medicine and Biology 17th Annual Scientific Session 2006:(Abstract submitted).

The invention claimed is:

1. A method of applying a treatment to a tissue of a subject capable of ameliorating a disorder of the subject, the method comprising:
(A) determining a first physiological state of the tissue by using a hyperspectral imaging device to obtain a first hyperspectral image of the tissue while said tissue is not subject to a pressure or weight;
(B) applying a pressure or weight to the tissue;
(C) determining a second physiological state of the tissue by using a hyperspectral imaging device to obtain a second hyperspectral image of the tissue while said tissue is subject to the pressure or weight;
(D) identifying areas of the tissue or corresponding aspects of the pressure or weight that can be modified to reduce the difference between the first and second physiological states, wherein the identifying (D) comprises registering the first hyperspectral image to the second hyperspectral image and wherein the identifying (D) thereby specifies non-uniform application of the pressure or weight to the tissue, wherein the first and second physiologic states comprise tissue oxygenation, oxygen extraction, tissue metabolism, or tissue perfusion; and
(E) applying a treatment regimen to the subject based on the identification of the areas of the tissue or corresponding aspects of the pressure or weight that can be modified to reduce the difference between the first and second physiological states.

2. The method of claim 1, wherein said identifying (D) comprises comparing the first image with the second image.

3. The method of claim 1, wherein the tissue is of a toe, a foot, a leg, a finger, a hand, an arm, or any portion thereof.

4. The method of claim 1, wherein the pressure or weight comprises pressure exerted on the tissue from a prosthetic device.

5. The method of claim 4, wherein the prosthetic device is selected from the group consisting of a toe prosthesis, a foot prosthesis, a hand prosthesis, a finger prosthesis, a leg prosthesis, and an arm prosthesis.

6. The method of claim 1, wherein said determining (C) further comprises determining a pressure load by obtaining a hyperspectral or multispectral tissue map.

7. The method of claim 1, wherein the treatment regimen comprises modifying the areas of the tissue or the corresponding aspects of the pressure or weight to reduce the difference between the first and second physiological states.

8. The method of claim 7, wherein said modification includes altering a structure of a prosthetic device, a compression stocking, a bandage, or a tissue wrap.

9. The method of claim 8, wherein altering the structure of the prosthetic device comprises adding or removing cushioning material.

10. The method of claim 9, wherein the adding or removing cushioning prevents or reduces ulceration or tissue breakdown attributable to the prosthetic device.

11. The method of claim 1
wherein the treatment regimen comprises modifying a prosthetic device to reduce the pressure or weight on the identified areas of the tissue caused by the prosthetic device.

12. The method of claim 1, wherein said tissue comprises a sole of a foot, and wherein said identifying (D) comprises generating a hyperspectral gradient map that indicates differences between the first and second physiological states across the sole of the foot; wherein
the treatment regimen comprises redistributing pressures across the sole to reduce pressure on areas deemed to be at risk areas or areas with large differences between the first and second physiological states.

13. The method of claim 12, wherein the pressures are redistributed across the sole by a tailored device that reduces pressure in a wound or at risk skin areas to less than zero.

14. The method of claim 1, wherein said identifying comprises generating a hyperspectral gradient map that indicates differences between the first and second physiological states across the tissue; wherein
the treatment regimen comprises redistributing pressure across the tissue to reduce pressure on at risk areas or areas with large differences between the first and second physiological states.

15. The method of claim 1, further comprising identifying at risk areas by:
comparing changes in oxygenation levels of the tissue over a period of time.

16. The method of claim 1, further comprising identifying at risk areas by comparing changes in oxygenation levels of the tissue when said tissue is not subjected to the pressure or weight.

17. The method of claim 16, wherein the tissue comprises a foot of the subject and the pressure or weight comprises the subject's body weight.

18. The method of claim 1, wherein the treatment regimen comprises modifying the areas of the tissue or the corresponding aspects of the pressure or weight to increase the difference between the first and second physiological states.

19. The method of claim 18, wherein said modification includes altering a structure of a prosthetic device, a compression stocking, a bandage, or a tissue wrap.

20. The method of claim 1, further comprising:
determining a map of pressure exerted across the tissue while said tissue is subjected to the pressure or weight; and
co-registering the map of pressure exerted across the tissue to the first and second hyperspectral images.

21. The method of claim 20, wherein said identifying (D) comprises identifying areas of the tissue most at risk for ulcer formation or progression,
wherein the treatment regimen comprises modifying the identified areas of the tissue or the corresponding aspects of the pressure or weight to reduce the difference between the first and second physiological states at the identified area, wherein modification includes altering a structure of a prosthetic device, a compression stocking, a bandage, or a tissue wrap.

22. The method of claim 21, wherein:
the treatment regimen comprises using hyperspectral information from the hyperspectral images to reduce pressure to the areas of the tissue identified to be at risk; and
using pressure information from the map of pressure exerted across the tissue to redistribute the pressure reduced from the areas of the tissue identified to be at risk to the surrounding tissue.

* * * * *